(12) United States Patent
Hamamoto et al.

(10) Patent No.: US 10,829,514 B2
(45) Date of Patent: Nov. 10, 2020

(54) VIRUS REMOVAL MEMBRANE

(71) Applicant: ASAHI KASEI MEDICAL CO., LTD., Tokyo (JP)

(72) Inventors: Ryo Hamamoto, Tokyo (JP); Tomoko Hongo, Tokyo (JP); Fujiharu Nagoya, Tokyo (JP)

(73) Assignee: ASAHI KASEI MEDICAL CO., LTD., Tokyo (JP)

( * ) Notice: Subject to any disclaimer, the term of this patent is extended or adjusted under 35 U.S.C. 154(b) by 0 days.

(21) Appl. No.: 15/302,269

(22) PCT Filed: Apr. 10, 2015

(86) PCT No.: PCT/JP2015/061288
§ 371 (c)(1),
(2) Date: Oct. 6, 2016

(87) PCT Pub. No.: WO2015/156403
PCT Pub. Date: Oct. 15, 2015

(65) Prior Publication Data
US 2017/0029462 A1 Feb. 2, 2017

(30) Foreign Application Priority Data

Apr. 11, 2014 (JP) .................................. 2014-082368
Jan. 16, 2015 (JP) .................................. 2015-007073

(51) Int. Cl.
*C07K 1/34* (2006.01)
*B01D 71/78* (2006.01)
(Continued)

(52) U.S. Cl.
CPC ............. *C07K 1/34* (2013.01); *B01D 67/0093* (2013.01); *B01D 69/02* (2013.01); *B01D 69/08* (2013.01);
(Continued)

(58) Field of Classification Search
None
See application file for complete search history.

(56) References Cited

U.S. PATENT DOCUMENTS 4,975,190 A 12/1990 Sakashita et al.
5,789,081 A 8/1998 Komatsu et al.
(Continued)

FOREIGN PATENT DOCUMENTS

EP 0 747 113 12/1996
EP 2199319 6/2010
(Continued)

OTHER PUBLICATIONS

Search Report issued in Japan Patent Application No. PCT/JP2015/061288, dated Jun. 9, 2015.
(Continued)

*Primary Examiner* — Krishnan S Menon
(74) *Attorney, Agent, or Firm* — Greenblum & Bernstein, P.L.C.

(57) ABSTRACT

A virus removal membrane is formed from a hydrophilized synthetic polymer, in which, when a solution containing gold colloids having a diameter of 20 nm is applied through a primary surface to the virus removal membrane to allow the virus removal membrane to capture the gold colloids for measurement of brightness in a cross section of the virus removal membrane, a value obtained by dividing a standard deviation of a value of an area of a spectrum of variation in the brightness by an average of the value of the area is 0.01 or more and 1.5 or less; and a thickness of a portion, where gold colloids having a diameter of 20 nm or more and 30 nm or less are captured, in the cross section of the virus removal membrane in a wet state is 10 μm or more and 30 μm or less.

16 Claims, 6 Drawing Sheets

(51) Int. Cl.
  *B01D 69/02* (2006.01)
  *B01D 69/08* (2006.01)
  *B01D 67/00* (2006.01)
  *B01D 69/12* (2006.01)
  *B01D 71/02* (2006.01)
  *B01D 71/06* (2006.01)
  *C08J 7/16* (2006.01)
  *C08J 9/00* (2006.01)
  *C08J 9/14* (2006.01)
  *C08J 9/36* (2006.01)
  *C08K 5/12* (2006.01)
  *B01D 69/06* (2006.01)
  *B01D 71/34* (2006.01)

(52) U.S. Cl.
  CPC ........... *B01D 69/087* (2013.01); *B01D 69/12* (2013.01); *B01D 71/022* (2013.01); *B01D 71/06* (2013.01); *B01D 71/78* (2013.01); *C08J 7/16* (2013.01); *C08J 9/0023* (2013.01); *C08J 9/142* (2013.01); *C08J 9/36* (2013.01); *C08K 5/12* (2013.01); *B01D 69/06* (2013.01); *B01D 71/34* (2013.01); *B01D 2323/02* (2013.01); *B01D 2323/08* (2013.01); *B01D 2323/38* (2013.01); *B01D 2325/022* (2013.01); *B01D 2325/04* (2013.01); *B01D 2325/20* (2013.01); *B01D 2325/38* (2013.01); *C08J 2203/12* (2013.01); *C08J 2207/00* (2013.01); *C08J 2327/16* (2013.01)

(56) References Cited

U.S. PATENT DOCUMENTS

| | | |
|---|---|---|
| 6,797,169 B1 | 9/2004 | Ide et al. |
| 2004/0023017 A1 | 2/2004 | Nagoya et al. |
| 2006/0016748 A1 | 1/2006 | Koguma et al. |
| 2009/0145831 A1* | 6/2009 | Manabe ............... B01D 63/082 210/232 |
| 2010/0096328 A1* | 4/2010 | Hamasaki ............ B01D 65/102 210/638 |
| 2010/0147763 A1 | 6/2010 | Tsou et al. |
| 2012/0305472 A1 | 12/2012 | Yokota et al. |
| 2015/0232506 A1 | 8/2015 | Ashitaka et al. |

FOREIGN PATENT DOCUMENTS

| | | |
|---|---|---|
| GB | 2 221 917 | 2/1990 |
| JP | 1-148305 | 6/1989 |
| JP | 4-371221 | 12/1992 |
| JP | 5-000233 | 1/1993 |
| JP | 2008-272636 | 11/2008 |
| JP | 2010-14564 | 1/2010 |
| JP | 2011-136305 | 7/2011 |
| JP | 2012-91154 | 5/2012 |
| JP | 2013-71100 | 4/2013 |
| JP | 5403444 | 11/2013 |
| WO | 01/14047 | 3/2001 |
| WO | 03/026779 | 4/2003 |
| WO | 2004/035180 | 4/2004 |
| WO | 2011/111679 | 9/2011 |
| WO | 2013/012024 | 1/2013 |

OTHER PUBLICATIONS

International Preliminary Report on Patentability in Japan Patent Application No. PCT/JP2015/061288, dated Oct. 12, 2016.
Written Opinion of the International Search Authority in Japan Patent Application No. PCT/JP2015/061288 and translation thereof, dated Jun. 9, 2015.
Search Report issued in European Patent Office (EPO) Patent Application No. 15776880.5, dated Apr. 18, 2017.

* cited by examiner

Fig. 5

| | | | Example 1 | Example 2 | Example 3 | Example 4 | Example 5 | Example 6 | Example 7 | Example 8 | Example 9 | Example 10 | Example 11 |
|---|---|---|---|---|---|---|---|---|---|---|---|---|---|
| Manufacturing Conditions | Hollowing Agent Inlet Temperature | °C | 95.0 | 80.0 | 62.5 | 80.0 | 62.5 | 62.5 | 62.5 | 55.0 | 80.0 | 62.5 | 62.5 |
| | Hollowing Agent Outlet Temperature | °C | 155.0 | 150.0 | 140.0 | 150.0 | 140.0 | 140.0 | 140.0 | 135.0 | 150.0 | 140.0 | 140.0 |
| | Difference in Hollowing Agent Temperature (Outlet - Inlet) | °C | 60.0 | 70.0 | 77.5 | 70.0 | 77.5 | 77.5 | 77.5 | 80.0 | 70.0 | 77.5 | 77.5 |
| | Coagulating Bath Temperature | °C | 21.0 | 22.0 | 25.0 | 25.5 | 25.0 | 26.0 | 26.0 | 30.0 | 24.0 | 26.0 | 30.0 |
| | Air Gap | mm | 200 | 150 | 100 | 50 | 50 | 50 | 50 | 50 | 30 | 30 | 30 |
| Physical Properties | Graft Ratio | % | 8.7 | 10.1 | 8.8 | 9.6 | 9.5 | 10.1 | 10.2 | 9.5 | 9.5 | 9.1 | 9.0 |
| | Inner Diameter | μm | 340.0 | 329.0 | 328.0 | 337.0 | 334.0 | 335.0 | 327.0 | 329.0 | 329.0 | 327.0 | 328.0 |
| | Thickness | μm | 45.0 | 48.0 | 46.0 | 48.0 | 48.0 | 45.0 | 48.0 | 48.0 | 43.0 | 43.5 | 43.2 |
| | Bubble Point | MPa | 1.80 | 1.73 | 1.60 | 1.59 | 1.57 | 1.50 | 1.51 | 1.40 | 1.50 | 1.46 | 1.38 |
| | Pure Water Permeation Rate | L/m²/hrs/0.1MPa | 33 | 35 | 38 | 43.9 | 40 | 46 | 44 | 54.8 | 45 | 50 | 54 |
| Evaluations | Thickness of Dense Layer | μm | 10.4 | 10.0 | 10.1 | 15.2 | 15.1 | 16.4 | 13.9 | 17.2 | 25.0 | 26.4 | 24.8 |
| | Variation Coefficient of Amount of Captured Gold Colloids | | 0.28 | 0.50 | 0.80 | 0.39 | 0.59 | 0.44 | 0.73 | 1.30 | 0.32 | 0.66 | 0.87 |
| | Thickness of Densest Layer | μm | 9.6 | 8.8 | 7.7 | 7.8 | 4.6 | 3.4 | 3.6 | 3.4 | 3.7 | 2.8 | 2.4 |
| | First Attainment Level | 30 nm, % | 37.42 | 38.43 | 36.44 | 28.41 | 34.42 | 30.43 | 30.41 | 29.41 | 16.41 | 16.40 | 20.39 |
| | Second Attainment Level | 20 nm, % | 39.63 | 40.62 | 43.60 | 36.65 | 43.69 | 42.70 | 41.63 | 40.70 | 43.77 | 45.80 | 43.79 |
| | | 15 nm, % | 74.98 | 78.99 | 80.99 | 76.95 | 87.98 | 90.98 | 89.97 | 90.98 | 89.98 | 93.100 | 93.99 |
| | Logarithmic Removal Rate of Gold Colloid | 30 nm, LRV | ≥1.40 | ≥1.40 | ≥1.40 | ≥1.40 | ≥1.40 | ≥1.40 | ≥1.40 | ≥1.40 | ≥1.40 | ≥1.40 | ≥1.40 |
| | | 20 nm, LRV | ≥1.40 | ≥1.40 | ≥1.40 | ≥1.40 | ≥1.40 | ≥1.40 | ≥1.40 | ≥1.40 | ≥1.40 | ≥1.40 | ≥1.40 |
| | | 15 nm, LRV | ≥1.40 | 0.03 | 0.07 | 0.07 | 1.20 | 1.10 | 0.92 | 0.50 | 0.60 | 0.40 | 0.30 |
| | | 10 nm, LRV | 0.09 | 0.03 | 0.07 | 0.07 | 0.05 | 0.05 | 0.05 | 0.04 | 0.04 | 0.04 | 0.03 |
| Effects | Virus Removal Property | LRV | ≥6.00 | ≥6.00 | ≥6.00 | ≥6.00 | ≥6.00 | ≥6.00 | ≥6.00 | ≥6.00 | ≥6.00 | ≥6.00 | ≥6.00 |
| | Lrv of Stop & Start | LRV | ≥6.00 | ≥6.00 | ≥6.00 | ≥6.00 | ≥6.00 | 5.00 | 4.70 | 4.50 | 4.50 | 4.30 | 4.10 |
| | Maximum Capture Capacity | Log₁₀(TCID₅₀/m²) | ≥14.0 | 13.8 | 13.5 | 13.5 | 13.3 | 13.1 | 12.8 | 12.3 | 12.5 | 12.2 | 11.8 |
| | Flux decay | % | — | — | 25 | — | — | 18 | — | — | 13 | — | — |

Fig. 6

| | | | Comparative Example 1 | Comparative Example 2 | Comparative Example 3 |
|---|---|---|---|---|---|
| Manufacturing Conditions | Hollowing Agent Inlet Temperature | °C | 62.5 | 62.5 | 30.0 |
| | Hollowing Agent Outlet Temperature | °C | 140.0 | 140.0 | 120.0 |
| | Difference In Hollowing Agent Temperature (Outlet - Inlet) | °C | 77.5 | 77.5 | 90.0 |
| | Coagulating Bath Temperature | °C | 20.0 | 35.0 | 26.0 |
| | Air Gap | mm | 400 | 10 | 50 |
| Physical Properties | Graft Ratio | % | 9.2 | 9.7 | 10.0 |
| | Inner Diameter | μm | 338.0 | 342.0 | 329.0 |
| | Thickness | μm | 43.0 | 48.0 | 45.0 |
| | Bubble Point | MPa | 1.90 | 1.29 | 1.40 |
| | Pure Water Permeation Rate | L/m²/hrs/0.1MPa | 20 | 70 | 45 |
| Evaluations | Thickness of Dense Layer | μm | 8.8 | 34.8 | 15.2 |
| | Variation Coefficient of Amount of Captured Gold Colloids | | 0.85 | 0.92 | 1.70 |
| | Thickness of Densest Layer | μm | 10.8 | 1.7 | 4.0 |
| | First Attainment Level, Second Attainment Level | 30 nm | 38~43 | 5~38 | 32~41 |
| | | 20 nm | 40~59 | 40~86 | 41~69 |
| | | 15 nm | 75~99 | 94~98 | 85~97 |
| | Logarithmic Removal Rate of Gold Colloid | 30 nm LRV | ≥1.40 | ≥1.40 | ≥1.40 |
| | | 20 nm LRV | ≥1.40 | ≥1.40 | ≥1.40 |
| | | 15 nm LRV | ≥1.4 | 0.09 | 0.20 |
| | | 10 nm LRV | 0.13 | 0.03 | 0.05 |
| Effects | Virus Removal Property | LRV | ≥6.00 | 5.00 | 5.50 |
| | Lrv of Stop & Start | LRV | ≥6.00 | 2.30 | 3.50 |
| | Maximum Capture Capacity | Log₁₀(TCID₅₀/m²) | Clogging in Filtration | 10.5 | 11.0 |
| | Flux decay | % | 80 | — | — |

VIRUS REMOVAL MEMBRANE

TECHNICAL FIELD

The present invention relates to a virus removal membrane for removing viruses from a solution.

BACKGROUND ART

In recent years, a measure to enhance virus safety has been necessary for not only plasma derivatives derived from human blood, but also bio-pharmaceuticals. Therefore, pharmaceutical manufacturers have studied to introduce a virus removal/inactivation step in a manufacturing process. In particular, a virus removal method by filtration with a virus removal membrane is an effective method that can provide virus reduction without denaturing useful proteins.

Among viruses, in particular, parvovirus has been reported with respect to a case of infection with human parvovirus B19 in the field of plasma derivatives, and a case of contamination of CHO (Chinese Hamster Ovary) cells with mouse parvovirus in the bio-pharmaceutical field. Parvovirus, which is a small virus, has no envelope, and it is thus physicochemically stable and is resistant to heating, a low pH and a treatment with a chemical agent which correspond to an inactivation step generally performed during a pharmaceutical manufacturing process. Therefore, there is a growing need for parvovirus removal by a virus removal membrane, as a virus removal method having a different mechanism from that of an inactivation method.

Patent Literature 1 discloses a porous hollow fiber membrane for treating a protein-containing liquid, wherein the membrane is made of a porous hollow fiber including a hydrophobic polymer and a hydrophilic polymer, and has a capture layer in the vicinity of each of the inner periphery and the outer periphery of a membrane thickness portion. In Patent Literature 1, a membrane structure is evaluated by subjecting gold colloid particles having a size comparable with a virus size to filtration by the hollow fiber membrane, and observing the cross section of the membrane by an optical microscope. Patent Literature 1, however, discloses no specific evaluation method and the like with respect to a membrane of the material of polyvinylidene fluoride, which is a thermoplastic crystalline polymer, for the reason that a complicated step is included in order to impart hydrophilicity.

Patent Literature 2 discloses an integrity test method of a separation membrane in which a dispersion liquid of metal particles or metal compound particles having an average particle size of 10 to 30 nm is used. However, with respect to membranes of polysulfone, polyether sulfone, polyvinylidene fluoride resins, or the like, Patent Literature 2 discloses evaluation of only hydrophobic membranes thereof not subjected to a chemical hydrophilization treatment such as graft polymerization.

Patent Literature 3 discloses a microporous membrane having a coarse structure layer having a high aperture rate and a dense structure layer having a low aperture rate, wherein the microporous membrane has sufficient virus removal performance and is prominently permeable to physiologically active substances such as proteins. Patent Literature 3, however, merely discloses a two-layer structure of the coarse structure layer and the dense structure layer as the structure in the thickness direction of the membrane, and discloses neither the change in pore size in the thickness direction of the dense structure layer, nor the membrane structure in the periphery direction.

On the other hand, a virus removal membrane having high virus removal properties with respect to small viruses (for example, parvovirus) having a size close to the size of useful proteins and also having high protein filtration efficiency has been demanded in the pharmaceutical manufacturing site, and the demand for a virus removal membrane has been increasingly severe year by year.

In view of the above, the total amount of viruses to be loaded to a virus removal membrane (the amount of viruses to be spiked to a pharmaceutical protein, or the total amount thereof to be filtered off) has been increased in a virus removal membrane evaluation test in which the capacity of a virus removal step in a pharmaceutical manufacturing process is examined, and conditions for passing the virus removal membrane evaluation test have been increasingly severe year by year.

Furthermore, in a pharmaceutical manufacturing process, a virus removal membrane is often used usually for dead-end type filtration at a constant pressure or at a constant flow velocity, and it is important to control the pressure (flow velocity) as a parameter of the process. The pressure (flow velocity), however, may be turned ON or OFF, or the pressure (flow velocity) level may be changed. Specific examples include the following cases.

(1) A case where filtration is performed at a reduced pressure (flow velocity) level in order to suppress clogging of a virus removal membrane and increase the permeability to a pharmaceutical protein depending on properties of the protein.

(2) A case where, after filtration of a pharmaceutical protein, a step of temporarily interrupting filtration for washing with a buffer for the purpose of recovering a pharmaceutical protein remaining in a virus removal membrane (Post-wash) is included.

(3) A case where filtration is temporarily interrupted due to an event such as power outage, followed by repressurizing the membrane (Stop & start).

In any of cases (1) to (3) above, degradation of virus removal capability may be observed. Therefore, there is increasingly a need for a membrane that is less degraded in virus removal capability even when the pressure (flow velocity) is turned ON or OFF and/or the pressure (flow velocity) level is changed.

CITATION LIST

Patent Literature

Patent Literature 1: Japanese Patent Laid-Open No. 2013-071100
Patent Literature 2: Japanese Patent Laid-Open No. 2011-136305
Patent Literature 3: International Publication No. WO 03/026779

SUMMARY OF INVENTION

Technical Problem

It has, however, been conventionally difficult to maintain high filtration efficiency while maintaining high virus removal performance. One object of the present invention is then to provide a virus removal membrane having high virus removal capability and filtration efficiency.

Solution to Problem

An aspect of the present invention provides a virus removal membrane for removing viruses from a protein-containing solution, the virus removal membrane including a primary surface to which the protein-containing solution is applied, and a secondary surface from which a liquid that permeates through the virus removal membrane is flowed, wherein, when a solution containing gold colloids having a diameter of 20 nm is applied through the primary surface to the virus removal membrane to allow the virus removal membrane to capture the gold colloids for measurement of brightness in a cross section of the virus removal membrane, a value obtained by dividing a standard deviation of a value of an area of a spectrum of variation in the brightness by an average of the value of the area of the spectrum of variation in the brightness is 0.01 or more and 1.50 or less; a thickness of a portion where gold colloids having a diameter of 20 nm or more and 30 nm or less are captured in the cross section of the virus removal membrane in a wet state is 10 μm or more and 30 μm or less; and the virus removal membrane is formed of a hydrophilized synthetic polymer.

For example, a portion where gold colloids having a diameter of 30 nm are captured is located at a place corresponding to 15% or more and 60% or less of a thickness of the virus removal membrane from the primary surface, a portion where gold colloids having a diameter of 20 nm are captured is located at a place corresponding to 25% or more and 85% or less of the membrane thickness from the primary surface, and a portion where gold colloids having a diameter of 15 nm are captured is located at a place corresponding to 60% or more and 100% or less of the membrane thickness from the primary surface, in the cross section of the virus removal membrane in a wet state.

For example, the virus removal membrane does not capture gold colloids having a diameter of 10 nm. In addition, for example, in the virus removal membrane, a logarithmic removal rate of gold colloid having a diameter of 30 nm is 1.00 or more, a logarithmic removal rate of gold colloid having a diameter of 20 nm is 1.00 or more, a logarithmic removal rate of gold colloid having a diameter of 15 nm is 0.10 or more, and a logarithmic removal rate of gold colloid having a diameter of 10 nm is less than 0.10. For example, a pore size is decreased and is then constant, from the primary surface towards the secondary surface in the cross section of the virus removal membrane, and the virus removal membrane preferably has a densest layer in the vicinity of the secondary surface. For example, the portion where gold colloids are captured in the virus removal membrane encompasses a portion where the pore size is a minimum value.

For example, a thickness of the virus removal membrane is 40.0 μm or more and 60.0 μm or less in a dry state. In addition, for example, a bubble point of the virus removal membrane is 1.30 MPa or more and 1.80 MPa or less, and a pure water permeation rate is 30 L/m$^2$/hrs/0.1 MPa, or more and 80 L/m$^2$/hrs/0.1 MPa, or less. The virus removal membrane may be a hollow fiber membrane or a flat membrane. For example, the virus removal membrane may include a thermoplastic crystalline resin. The virus removal membrane may include a hydrophilic graft chain.

Advantageous Effects of Invention

The present invention makes it possible to provide a virus removal membrane having high virus removal capability and filtration efficiency.

BRIEF DESCRIPTION OF DRAWINGS

FIG. 5 is a table showing manufacturing conditions and evaluation results of a virus removal membrane according to each Example of the present invention.

FIG. 6 is a table showing manufacturing conditions and evaluation results of a virus removal membrane according to each Comparative Example of the present invention.

DESCRIPTION OF EMBODIMENTS

Hereinafter, embodiments of the present invention are described. In the following description of drawings, the same or similar part is represented by the same or similar reference sign. The drawings, however, are schematic, and are not accurately illustrated by specific dimensions and the like. Accordingly, specific dimensions and the like are required to be understood in view of the following description, and any part whose dimension relationship and ratio are different among the drawings is, of course, included.

Figure 1:
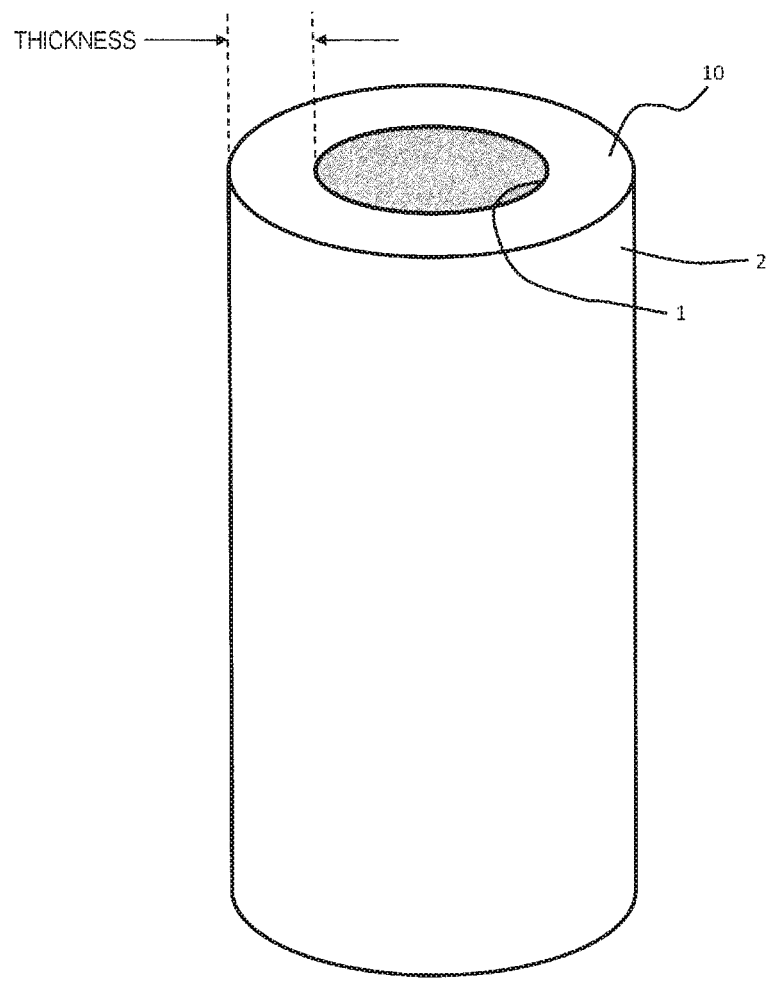
FIG. 1 is a schematic view of a virus removal membrane having a hollow fiber membrane shape, according to an embodiment of the present invention.

As illustrated in FIG. 1, a virus removal membrane 10 for removing viruses from a protein-containing solution, according to an embodiment, includes a primary surface 1 to which the protein-containing solution is applied, and a secondary surface 2 from which a liquid that permeates through the virus removal membrane 10 is flowed.

Figure 2:
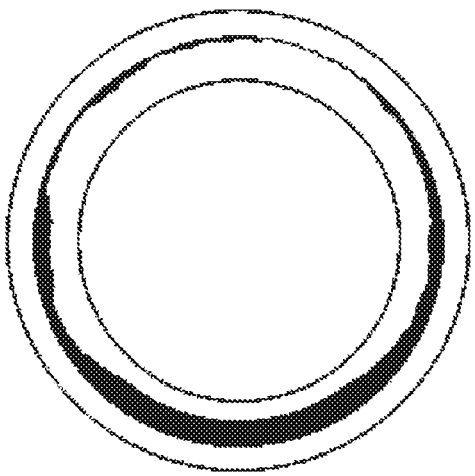
FIG. 2 is a schematic view of a virus capture portion in a virus removal membrane having a hollow fiber membrane shape, according to Reference Example of the present invention.
Figure 3:
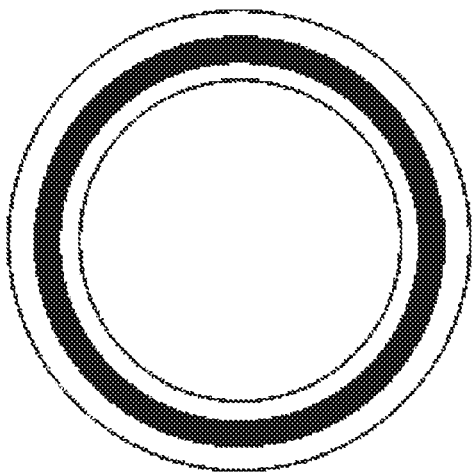
FIG. 3 is a schematic view of a virus capture portion in a virus removal membrane having a hollow fiber membrane shape, according to an embodiment of the present invention.

Small viruses to be removed by the virus removal membrane 10 have a diameter of, for example, 10 to 30 nm, or 18 to 24 nm. Specific examples of the viruses include parvovirus. Parvovirus has a diameter of about 20 nm. The virus removal membrane 10 has a virus capture portion, where viruses are captured, in the cross section thereof. The amount of viruses captured on the virus capture portion in the cross section is preferably uniform regardless of a point on a filtration surface (primary surface 1) which the solution enters. The reason for this is because, if the amount of viruses captured in the virus removal membrane is ununiform depending on a point on the filtration surface, the solution is concentrated at certain point on the filtration surface to partially increase the amount of viruses to be loaded at the point and thus viruses may be leaked from the point in a large capacity filtration under a high pressure condition. When the virus removal membrane 10 has a hollow fiber membrane shape, the amount of viruses captured on the virus capture portion is not ununiform as illustrated in FIG. 2, but preferably uniform as illustrated in FIG. 3, in the periphery direction.

Furthermore, in the virus removal membrane 10, the thickness of the virus capture portion is preferably uniform in the virus capture portion. When the virus removal membrane 10 has a hollow fiber membrane shape, the thickness of the virus capture portion is preferably uniform in the periphery direction. When the thickness of the virus capture portion is uniform, the solution can be uniformly spread in the periphery direction to result in reduction in virus leakage.

Here, it may be difficult to visually detect a virus captured by the virus removal membrane 10. On the contrary, a gold colloid does not allow light to transmit while it has a diameter comparable with a size of a virus, and therefore it is visually detected easily. Therefore, characteristics of the virus removal membrane 10 can be evaluated by, for example, filtering a gold colloid-containing solution by the virus removal membrane 10, and thereafter measuring the relative brightness of a gold colloid capture portion, where gold colloids are captured by the virus removal membrane 10, in the cross section of the virus removal membrane 10.

With respect to the virus removal membrane 10 according to the embodiment, when a solution containing gold colloids having a diameter of 20 nm is applied through the primary surface 1 to the virus removal membrane 10 to allow the virus removal membrane 10 to capture the gold colloids for measurement of brightness in the cross section of the virus removal membrane 10, the value obtained by dividing the standard deviation of the value of the area of the spectrum of variation in the brightness by the average of the value of the area of the spectrum of variation in the brightness is 0.01 or more and 1.50 or less. The value means the variation coefficient of the amount of gold colloids captured in the virus removal membrane 10, and a smaller value means higher uniformity of the amount of gold colloids captured on the gold colloid capture portion in the virus removal membrane 10.

In the virus removal membrane 10 according to the embodiment, the value indicating the variation coefficient is 0.01 or more and 1.50 or less, 0.01 or more and 1.20 or less, 0.01 or more and 1.00 or less, 0.01 or more and 0.90 or less, or 0.01 or more and 0.80 or less. The measurement limit of the variation coefficient is less than 0.01. A variation coefficient of more than 1.50 may cause the solution to be concentrated at at least certain one point in the periphery direction of the membrane to thereby result in virus leakage.

A variation coefficient of 0.01 or more and 1.50 or less can allow viruses to be uniformly captured on the virus capture portion of the membrane (in the periphery direction with respect to a hollow fiber membrane), and allow high virus removal performance to be maintained even in the case of an increase in the total amount of viruses to be loaded to the virus removal membrane (the amount of viruses to be spiked to a pharmaceutical protein, or the total amount thereof to be filtered off).

The variation coefficient is measured by, for example, the following method. A piece is cut out from the virus removal membrane applied to filtration of a gold colloid solution, and the brightness profile at each of a plurality of points in a part stained by gold colloids in the cross section of the piece is measured by an optical microscope. The gold colloids absorb light and therefore variation in the brightness depends on the amount of the captured gold colloids. Herein, a background noise may be, if necessary, removed from the brightness profile. Thereafter, a graph with the thickness represented on the horizontal axis and variation in the brightness represented on the vertical axis is created, and the area of the spectrum of variation in the brightness presented on the graph is calculated. Furthermore, the value obtained by dividing the standard deviation of the area of the spectrum of variation in the brightness at the plurality of points by the average of the area of the spectrum of variation in the brightness at the plurality of points is calculated as the value indicating the variation coefficient of the amount of gold colloids captured on the gold colloid capture portion in the virus removal membrane 10.

The thickness of a portion (dense layer), where gold colloids having a diameter of 20 nm or more and 30 nm or less are captured, in the cross section of the virus removal membrane 10 in a wet state is 10 µm or more and 30 µm or less, 10 µm or more and 29 µm or less, 10 µm or more and 28 µm or less, 10 µm or more and 20 µm or less, 11 µm or more and 20 µm or less, or 12 µm or more and 20 µm or less. When a thickness of the portion where the gold colloids having the diameter of 20 nm or more and 30 nm or less are captured is more than 30 µm, it indicates that a pore having a large pore size, through which the gold colloids having the diameter of 20 nm or more and 30 nm or less can pass, is present in a large number, and that the pore size distribution is thus broad. Therefore, the possibility of virus leakage is increased at a low filtration pressure (flow velocity) and/or in Stop & start or Post-wash including pressure release. On the other hand, when a thickness of the portion where the gold colloids having the diameter of 20 nm or more and 30 nm or less are captured is less than 10 µm, it indicates that a pore through which the gold colloids having the diameter of 20 nm or more and 30 nm or less can pass is present in a small number, and that the pore size distribution is thus narrow. Therefore, clogging of proteins and the like may occur in a narrow region to thereby increase a reduction in filtration rate during filtration, resulting in a reduction in final throughput, and thus such a thickness is not preferable.

The thickness of the portion where the gold colloids having the diameter of 20 nm or more and 30 nm or less are captured is obtained by, for example, the following method. A piece is cut out from the virus removal membrane applied to filtration of each of respective solutions of gold colloids having diameters of 20 nm and 30 nm. The brightness profile at each of a plurality of points in a part stained by the gold colloids in the cross section of the piece is measured by an optical microscope. Herein, a first distance "a" from the primary surface 1 of the virus removal membrane 10 to a part on the gold colloid capture portion where is closest to the primary surface is measured in the thickness direction. In addition, a second distance "b" from the primary surface 1 of the virus removal membrane 10 to a part on the gold colloid capture portion where is closest to the secondary surface 2 is measured in the thickness direction.

Next, the value A (=a/c (expressed in percentage)) obtained by division of the first distance "a" by the thickness "c" of the wet virus removal membrane and expressed in percentage is calculated at each of the plurality of points, and the average of the value "A" at the plurality of points is calculated as a first attainment level. In addition, the value "B" (=b/c (expressed in percentage)) obtained by division of the second distance "b" by the thickness "c" of the wet virus removal membrane and expressed in percentage is calculated at each of the plurality of points, and the average of the value "B" at the plurality of points is calculated as a second attainment level.

Furthermore, as represented by the following expression (1), the value obtained by multiplication of the difference between the average "$B_{20}$" of the second attainment level in the virus removal membrane applied to capturing of the gold colloids having the diameter of 20 nm by filtration, and the average "$A_{30}$" of the first attainment level in the virus removal membrane applied to capturing of gold colloids having a diameter of 30 nm by filtration, by the average "$C_{AVE}$" of the average "$C_{20}$" of the thickness of the wet virus removal membrane applied to capturing of the gold colloids having the diameter of 20 nm by filtration and the average "$C_{30}$" of the thickness of the wet virus removal membrane applied to capturing of the gold colloids having the diameter of 30 nm by filtration is calculated as the thickness "T" of the portion, where the gold colloids having the diameter of 20 nm or more and 30 nm or less are captured, in the cross section of the virus removal membrane 10 in flowing of the gold colloids having the diameter of 20 nm and the gold colloids having the diameter of 30 nm. The thickness "T" of the gold colloid capture portion is also expressed as the thickness "T" of the dense layer of the virus removal membrane.

$$T = (B_{20} - A_{30}) \times C_{AVE} \quad (1)$$

In the above method, the portion where the gold colloids having the diameter of 20 nm or more and 30 nm or less are captured is determined as the thickness of a region between the first attainment position in the virus removal membrane applied to capturing of the gold colloids having the diameter of 30 nm by filtration and the second attainment position in the virus removal membrane applied to capturing of the gold colloids having the diameter of 20 nm by filtration, and it is confirmed that the gold colloids having the diameter of 20 nm or more and 30 nm or less, except for the margin of error, are captured within the region.

The thickness of a portion (densest layer), where gold colloids having a diameter of 15 nm are captured, in the cross section of the virus removal membrane 10 in a wet state is desirably 2 μm or more and 10 μm or less, more preferably 3 μm or more and 10 μm or less. When a thickness of such a gold colloid capture portion is more than 10 μm, efficiency of filtration of not only a gold colloid-containing solution, but also a virus-containing solution tends to be reduced. A thickness of less than 2 μm is not preferable because an increase in the total amount of viruses to be loaded to the virus removal membrane (the amount of viruses to be spiked to a pharmaceutical protein, or the total amount thereof to be filtered off) and variation in the filtration pressure along with operating may cause virus leakage.

The thickness of the portion where the gold colloids having the diameter of 15 nm are captured is obtained by, for example, the following method. A piece is cut out from the virus removal membrane applied to filtration of a solution of the gold colloids having the diameter of 15 nm. The brightness profile at each of a plurality of points in a part stained by the gold colloids in the cross section of the piece is measured by an optical microscope. Herein, a first distance "d" from the primary surface 1 of the virus removal membrane 10 to a part on the gold colloid capture portion where is closest to the primary surface is measured in the thickness direction. In addition, a second distance "e" from the primary surface 1 of the virus removal membrane 10 to a part on the gold colloid capture portion where is closest to the secondary surface 2 is measured in the thickness direction.

Next, the value "D" (=d/f (expressed in percentage)) obtained by division of the first distance "d" by the thickness "f" of the wet virus removal membrane and expressed in percentage is calculated at each of the plurality of points, and the average of the value "D" at the plurality of points is calculated as the first attainment level. In addition, the value "E" (=e/f (expressed in percentage)) obtained by division of the second distance "e" by the thickness "f" of the wet virus removal membrane and expressed in percentage is calculated at each of the plurality of points, and the average of the value "E" at the plurality of points is calculated as the second attainment level.

Furthermore, as represented by the following expression (2), the value obtained by multiplication of the difference between the average "E" of the second attainment level and the average "D" of the first attainment level by the average "F" of the thickness of the virus removal membrane subjected to filtration, in a wet state, is calculated as the thickness "T" of the portion, where the gold colloids having the diameter of 15 nm are captured, in the cross section of the virus removal membrane 10 in flowing of the gold colloids having a diameter of 15 nm. The thickness "T" of the portion, where the gold colloids having the diameter of 15 nm are captured, is also expressed as the thickness "T" of the densest layer of the virus removal membrane.

$$T = (E - D) \times F \quad (2)$$

When a solution containing the gold colloids having the diameter of 30 nm is filtered by the virus removal membrane 10, the portion where the gold colloids having the diameter of 30 nm are captured in the cross section of the virus removal membrane 10 in a wet state is located at a place corresponding to, for example, 15% or more and 60% or less, or 20% or more and 55% or less of the membrane thickness from the primary surface 1 in measurement with an optical microscope. A value of less than 15% of the membrane thickness causes viruses and impurities to be captured at a position closer to the primary surface of the membrane and clogging can more occur. A value of more than 60% of the membrane thickness causes the intended viruses to be captured at a position closer to the secondary surface of the membrane and thus the viruses cannot be sometimes captured. Herein, even when a small amount of the gold colloids having the diameter of 30 nm is captured in a region of less than 15% or more than 60% of the membrane thickness from the primary surface 1, a case where the absolute value of the spectrum of variation in the brightness, determined by subtracting the brightness profile measured from a constant (255) in measurement with an optical microscope, is 10% or less relative to the maximum of the absolute value of the spectrum can be regarded as being within the margin of error with respect of capturing of the gold colloids in the region in terms of virus removal ability of the virus removal membrane, and therefore the portion where the gold colloids having the diameter of 30 nm are captured can be regarded as being located at a place corresponding to 15% or more and 60% or less of the membrane thickness from the primary surface 1.

When a solution containing the gold colloids having the diameter of 20 nm is filtered by the virus removal membrane 10, a portion where the gold colloids having the diameter of 20 nm are captured in the cross section of the virus removal membrane 10 in a wet state is located at a place corresponding to, for example, 25% or more and 85% or less, or 30% or more and 85% or less of the membrane thickness from the primary surface 1 in measurement with an optical microscope. A value of less than 25% of the membrane thickness causes viruses and impurities to be captured at a position closer to the primary surface of the membrane and clogging can more occur. A value of more than 85% of the membrane thickness causes the intended viruses to be captured at a position closer to the secondary surface of the membrane and thus the viruses cannot be sometimes captured. Herein, even when the gold colloids are observed in a region of less than 25% or more than 85% of the membrane thickness from the primary surface 1 as in the case of the gold colloids having the diameter of 30 nm, a case where the absolute value of the spectrum of variation in the brightness, determined by subtracting the brightness profile measured from a constant (255) in measurement with an optical microscope, is 10% or less relative to the maximum of the absolute value of the spectrum can be regarded as being within the margin of error.

When a solution containing the gold colloids having the diameter of 15 nm is filtered by the virus removal membrane 10, a portion where the gold colloids having the diameter of 15 nm are captured in the cross section of the virus removal membrane 10 in a wet state is located at a place corresponding to, for example, 60% or more and 100% or less, or 65% or more and 100% or less of the membrane thickness from the primary surface 1 in measurement with an optical microscope. A value of less than 60% of the membrane thickness causes viruses and impurities to be captured at a position closer to the primary surface of the membrane and clogging can more occur. Herein, even when the gold colloids are observed in a region of less than 60% of the membrane thickness from the primary surface 1 as in the cases of respective gold colloids having diameters of 30 nm and 20 nm, a case where the absolute value of the spectrum of variation in the brightness, determined by subtracting the brightness profile measured from a constant (255) in measurement with an optical microscope, is 10% or less relative to the maximum of the absolute value of the spectrum can be regarded as being within the margin of error.

The capture position of each of respective gold colloids having diameters of 30 nm, 20 nm and 15 nm is consistently measured with respect to the gold colloids captured by the membrane. Accordingly, gold colloids that are not captured by the membrane and that permeate through the membrane are not subjected to such measurement. In other words, the capture position of every gold colloid allowed to permeate through the membrane is not measured, but the capture position of the gold colloids captured by the membrane, on the membrane, is measured.

When a solution containing gold colloids having a diameter of 10 nm is filtered by the virus removal membrane 10, almost no gold colloids having the diameter of 10 nm are captured in the cross section of the virus removal membrane 10. This can be confirmed from the following: the spectrum of the brightness cannot be significantly detected in observation using an optical microscope (Biozero, BZ 8100, manufactured by Keyence Corporation). This can also be confirmed from a reduction in a logarithmic removal rate (LRV) described later. Herein, no gold colloids having the diameter of 10 nm being captured indicate that a useful protein having a diameter of about 10 nm, such as IgG, can achieve high permeability.

The synthetic polymer as the material of the virus removal membrane is preferably a thermoplastic crystalline resin, which is easy of processing such as compression, extrusion, injection, inflation, and blow moldings, and is excellent in pressure resistance in filtration. In particular, a polyolefin resin and a fluororesin are preferable because of having heat resistance and molding processability in a well-balanced manner, and in particular, a polyvinylidene fluoride resin is preferable.

Herein, such a hydrophobic thermoplastic crystal resin causes adsorption of a protein and the like, and contamination, clogging and the like of the membrane to easily occur, resulting in a rapid reduction in filtration rate. Therefore, when a hydrophobic resin is used as the material of the virus removal membrane, hydrophilicity is imparted to the membrane in order to prevent occlusion due to adsorption of a protein and the like. In order to impart hydrophilicity, the membrane preferably has hydrophilic graft chains by a graft polymerization method.

Figure 4:
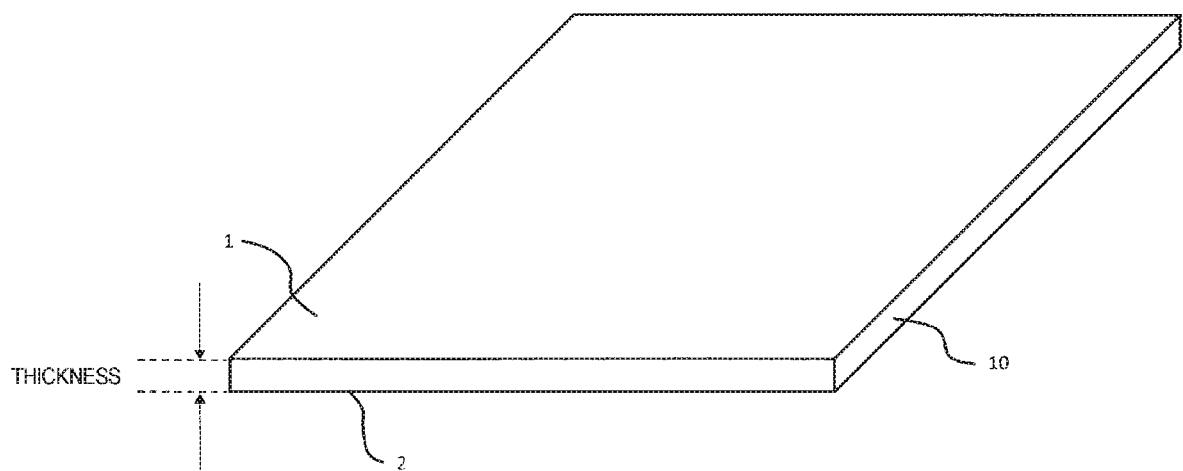
FIG. 4 is a schematic view of a virus removal membrane having a flat membrane shape, according to an embodiment of the present invention.

The virus removal membrane 10 has, for example, a hollow fiber membrane shape. Alternatively, the virus removal membrane 10 may have a flat membrane shape as illustrated in FIG. 4. The membrane is preferably a hollow fiber membrane, because it can be packed in a container to make a compact filter while having a large membrane area.

The thickness of the virus removal membrane 10 illustrated in FIG. 1 is, for example, 40.0 µm or more and 60.0 µm or less, more preferably 42.0 µm or more and 55.0 µm or less, in a dry state. A membrane thickness of less than 40.0 µm may result in a reduction in strength of the membrane to cause the membrane not to withstand the filtration pressure, and a thickness of more than 60.0 µm may result in a reduction in filtration rate.

The pore size of a pore is decreased and is then constant, from the primary surface towards the secondary surface in the cross section of the virus removal membrane 10, and the virus removal membrane 10 preferably has a densest layer in the vicinity of the outermost layer close to the secondary surface. When the virus removal membrane 10 has the densest layer in the vicinity of the outermost layer, virus leakage at a low filtration pressure (flow velocity) and/or in filtration in a Stop & start or Post-wash system can be reduced more.

The logarithmic removal rate (LRV: Logarithmic Reduction Value) of virus by the virus removal membrane 10 is preferably, for example, 4.00 or more because viruses are sufficiently removed by membrane filtration, and the logarithmic removal rate is more preferably 4.50 or more, 5.00 or more, or 6.00 or more. A logarithmic removal rate of virus of 6.00 or more is considered to allow viruses to be removed, resulting in almost no virus leakage.

The virus removal membrane 10 has a logarithmic removal rate (LRV) of gold colloid having a diameter of 30 nm, of, for example, 1.00 or more, preferably 1.20 or more. The virus removal membrane 10 has a logarithmic removal rate of gold colloid having a diameter of 20 nm, of, for example, 1.00 or more, preferably 1.20 or more. The virus removal membrane 10 has a logarithmic removal rate of gold colloid having a diameter of 15 nm, of, for example, 0.10 or more, preferably 0.20 or more. The virus removal membrane 10 has a logarithmic removal rate of gold colloid having a diameter of 10 nm, of, for example, less than 0.10.

The bubble point measured in the virus removal membrane 10 is, for example, 1.30 MPa or more and 1.80 MPa or less, more preferably 1.40 MPa or more and 1.80 MPa or less, 1.45 MPa or more and 1.80 MPa or less, or 1.50 MPa or more and 1.80 MPa or less. Characteristics of the virus removal membrane can also be expressed as the ratio of the bubble point (MPa) to the surface tension (N/m) of a solvent used for measurement. When hydrofluoroether, which has a surface tension of 13.6 mN/m, is used as a test liquid for immersion of the membrane, the ratio of the bubble point to the surface tension is 96 or more and 133 or less, more preferably 103 or more and 133 or less, 106 or more and 133 or less, or 110 or more and 133 or less.

A bubble point of 1.30 MPa or less indicates that pores having a large pore size are present, and is not preferable because degradation of virus removal capability is observed under conditions including (1) a step of reducing the pressure level, (2) a step of temporarily interrupting filtration to perform repressurizing (Stop & start), or (3) a step of temporarily interrupting filtration after filtration of pharmaceutical proteins, for washing with a Suffer (Post-wash), in particular, in use of a virus removal filter. A bubble point of 1.80 MPa or more indicates that pores having a small pore size are present, and is not preferable because pure water permeation rate decreases.

The pure water permeation rate measured in the virus removal membrane 10 is 30 L/m$^2$/hrs/0.1 MPa, or more and 80 L/m$^2$/hrs/0.1 MPa, or less, 30 L/m$^2$/hrs/0.1 MPa, or more and 60 L/m$^2$/hrs/0.1 MPa, or less, or 30 L/m$^2$/hrs/0.1 MPa, or more and 55 L/m$^2$/hrs/0.1 MPa, or less.

The virus removal membrane according to the embodiment, having characteristics described above, is manufactured by, for example, a method described below.

The thermoplastic resin for use as the material of the virus removal membrane according to the embodiment is, for example, a thermoplastic resin having crystallinity, for use in usual compression, extrusion, injection, inflation, and blow moldings. For example, polyolefin resins such as a polyethylene resin, a polypropylene resin and a poly-4-methyl-1-pentene resin, polyester resins such as a polyethylene terephthalate resin, a polybutylene terephthalate resin, a polyethylene terenaphthalate resin, a polybutylene naphthalate resin and a polycyclohexylenedimethylene terephthalate resin, polyamide resins such as nylon 6, nylon 66, nylon 610, nylon 612, nylon 11, nylon 12 and nylon 46, fluororesins such as a polyvinylidene fluoride resin, an ethylene/tetrafluoroethylene resin and a polychlorotrifluoroethylene resin, a polyphenylene ether resin, and a polyacetal resin can be used.

Among the above thermoplastic resins, a polyolefin resin and a fluororesin are preferable because of having heat resistance and molding processability in a well-balanced manner, and in particular, a polyvinylidene fluoride resin is preferable. The polyvinylidene fluoride resin here refers to a fluororesin that has a vinylidene fluoride unit in the basic backbone and is a resin commonly referred to as an abbreviation "PVDF". As such a polyvinylidene fluoride resin, a homopolymer of vinylidene fluoride (VDF), or a copolymer of one or more monomers selected from the monomer group consisting of hexafluoropropylene (HFP), pentafluoropropylene (PFP), tetrafluoroethylene (TFE), chlorotrifluoroethylene (CTFE) and perfluoromethyl vinyl ether (PFMVE) with vinylidene fluoride (VDF) can be used. The homopolymer and the copolymer can also be used as a mixture thereof. In the embodiment, it is preferable to use a polyvinylidene fluoride resin including 30 to 100% by weight of the homopolymer because a microporous membrane is enhanced in crystallinity to have a high strength, and it is further preferable to use only the homopolymer.

The average molecular weight of the thermoplastic resin for use in the embodiment is preferably 50000 to 5000000, more preferably 100000 to 2000000, further preferably 150000 to 1000000. While the average molecular weight refers to a weight average molecular weight obtained by gel permeation chromatography (GPC) measurement, it is generally difficult to perform accurate GPC measurement of a resin having an average molecular weight of more than 1000000, and the viscosity average molecular weight by the viscosity method can be thus adopted as an alternative. A weight average molecular weight of less than 50000 is not preferable because of causing melt tension in melt molding to be decreased to result in degradation of moldability or a reduction in mechanical strength of the membrane. A weight average molecular weight of more than 5000000 is not preferable because of making uniform melt kneading difficult.

The polymer concentration of the thermoplastic resin for use in the embodiment, in a composition including the thermoplastic resin and a plasticizer, is preferably 20 to 90% by weight, more preferably 30 to 80% by weight, most preferably 35 to 70% by weight. A polymer concentration of less than 20% by weight causes the following disadvantages: membrane formation ability is degraded and a sufficient mechanical strength is not achieved. In addition, the resulting microporous membrane has a large pore size for a membrane for virus removal to cause virus removal performance to be insufficient. A polymer concentration of more than 90% by weight causes the resulting microporous membrane to have a too small pore size and a low porosity, thereby resulting in reduction in filtration rate and not withstanding practical use.

As the plasticizer for use in the embodiment, a non-volatile solvent is used which, when mixed with the thermoplastic resin in the composition for producing a microporous membrane, can form a uniform solution at a temperature not lower than the crystal melting point of the resin. The non-volatile solvent here refers to a solvent having a boiling point of 250.0° C. or higher under the atmospheric pressure. The plasticizer may be generally in the form of a liquid or solid at an ordinary temperature of 20.0° C. A plasticizer of a so-called solid-liquid phase separation system, which has a thermally induced solid-liquid phase separation point at a temperature not lower than an ordinary temperature in cooling of the uniform solution with the thermoplastic resin, is preferably used in terms of manufacturing of a membrane for use in virus removal, which is small in pore size and has a homogeneous dense structure layer. Among plasticizers, some has a thermally induced liquid-liquid phase separation point at a temperature not lower than an ordinary temperature in cooling of the uniform solution with the thermoplastic resin, and when a plasticizer of a liquid-liquid phase separation system is used, the resulting microporous membrane generally tends to have a large pore size. The plasticizer used here may be a single substance or a mixture of a plurality of substances.

In the method of measuring the thermally induced solid-liquid phase separation point, the thermally induced solid-liquid phase separation point can be determined by using a composition including the thermoplastic resin and the plasticizer and having a predetermined concentration, melt kneaded in advance, as a sample, and measuring the exothermic peak temperature of the resin by thermal analysis (DSC). In the method of measuring the crystallization point of the resin, the crystallization point can be determined by using the resin melt kneaded in advance, as a sample, and similarly performing the thermal analysis.

The plasticizer to be preferably used in manufacturing of the membrane for use in virus removal, the membrane being small in pore size and having a homogeneous dense structure layer, includes a plasticizer disclosed in International Publication No. WO 01/28667. That is, such a plasticizer is a plasticizer having a phase separation point depression constant of the composition, defined by the following expression (3), of 0.0 to 40.0° C., preferably a plasticizer having a phase separation point depression constant of 1.0 to 35.0° C., further preferably a plasticizer having a phase separation point depression constant of 5.0 to 30.0° C. A phase separation point depression constant of more than 40.0° C. is not preferable because of resulting in reductions in homogeneity of the pore size and strength.

$$\alpha = 100 \times (Tc_0 - Tc)/(100 - C) \quad (3)$$

(wherein, $\alpha$ represents the phase separation temperature depression constant (° C.), $Tc_0$ represents the crystallization temperature (° C.) of the thermoplastic resin, $Tc$ represents the thermally induced solid-liquid phase separation point (° C.) of the composition, and C represents the concentration (% by weight) of the thermoplastic resin in the composition.)

For example, when a polyvinylidene fluoride resin is selected as the thermoplastic resin, dicyclohexyl phthalate (DCHP), diamyl phthalate (DAP), triphenyl phosphate (TPP), diphenylcresyl phosphate (CDP), tricresyl phosphate (TCP), and the like are particularly preferable.

In the embodiment, a first method of uniformly dissolving the composition including the thermoplastic resin and the plasticizer includes loading the resin into a continuous resin kneading apparatus such as an extruder, and introducing the plasticizer at any ratio while heating and melting the resin, for screw kneading, to provide a uniform solution. The resin to be loaded may be in any form of a powder, a granule and a pellet. When uniform dissolution is achieved by such a method, the plasticizer is preferably in the form of an ordinary temperature liquid. As the extruder, a single screw extruder, a twin different direction screw extruder, a twin same direction screw extruder, and the like can be used.

A second method of uniformly dissolving the composition including the thermoplastic resin and the plasticizer includes using a stirring apparatus such as a Henschel mixer to mix the resin and the plasticizer in advance for dispersing, and loading the resulting composition into a continuous resin kneading apparatus such as an extruder for melt kneading, to thereby provide a uniform solution. The composition to be loaded may be in the form of a slurry in the case where the plasticizer is an ordinary temperature liquid, or may be in the form of a powder or a granule in the case where the plasticizer is an ordinary temperature solid.

A third method of uniformly dissolving the composition including the thermoplastic resin and the plasticizer is a method of using a simple resin kneading apparatus such as a brabender or a mill, or a method of performing melt kneading within another batch type kneading vessel. The method includes a batch-wise step, and has the advantages of simplicity and high flexibility.

In the embodiment, the composition including the thermoplastic resin and the plasticizer is heated to a temperature not lower than the crystal melting point of the thermoplastic resin and uniformly dissolved, then extruded in the form of a flat membrane or a hollow fiber through a discharge port of a T-die, a circular die, an annular spinneret or the like, and then cooled and solidified to mold a membrane (step (a)). In step (a) of molding a membrane by cooling and solidifying, a dense structure layer is formed and a coarse structure layer is also formed with being adjacent to the membrane surface.

In the embodiment, while the composition including the thermoplastic resin and the plasticizer and uniformly heated to dissolve is discharged through the discharge port and taken over as a membrane through an air gap part at a taking-over rate so that the draft ratio defined by the following expression (4) is 1.0 or more and 12.0 or less, one surface of the membrane is brought into contact with a non-volatile liquid at 100.0° C. or higher, which can partially dissolve the thermoplastic resin, and other surface of the membrane is cooled to thereby form a coarse structure layer and a dense structure layer in the membrane.

$$\text{Draft ratio} = (\text{taking-over rate of membrane})/(\text{discharge rate of composition at discharge port}) \quad (4)$$

The draft ratio is preferably 1.5 or more and 9.0 or less, more preferably 1.5 or more and 7.0 or less. A draft ratio of less than 1.0 causes tension not to be applied to the membrane, resulting in degradation of moldability, and a draft ratio of more than 12.0 causes the membrane to be stretched and it tends to make it difficult to form a coarse structure layer having a sufficient thickness. The discharge rate of the composition at the discharge port, of the expression (4), is given by the following expression (5).

$$\text{Discharge rate of composition at discharge port} = (\text{volume of composition to be discharged per unit time})/(\text{area of discharge port}) \quad (5)$$

A preferable range of the discharge rate is 1 to 60 m/min, more preferably 3 to 40 m/min. A discharge rate of less than 1 m/min tends to not only cause productivity to be degraded, but also cause the problem of an increase in variation in the amount to be discharged to occur. On the contrary, a discharge rate of more than 60 m/min may cause turbulent flow to occur at the discharge port due to a large amount to be discharged, resulting in an unstable discharge state.

The taking-over rate can be set depending on the discharge rate, and is preferably 1 to 200 m/min, more preferably 3 to 150 m/min. A taking-over rate of less than 1 m/min tends to cause productivity and moldability to be degraded. A taking-over rate of more than 200 m/min tends to cause the cooling time to be shorter and cause the tension applied to the membrane to be increased, thereby easily resulting in breaking of the membrane.

A preferable method of forming the coarse structure layer includes extruding the composition including the thermoplastic resin and the plasticizer in the form of a flat membrane or a hollow fiber membrane through an extrusion port to form an uncured membrane, and bringing one surface of the uncured membrane into contact with a non-volatile liquid which can partially dissolve the thermoplastic resin. In such a case, the non-volatile liquid for contact is diffused in the membrane and the thermoplastic resin is partially dissolved to thereby form a coarse structure layer. The liquid which can partially dissolve the thermoplastic resin is here a liquid that can form a uniform solution in a condition of a temperature of 100.0° C. or higher when mixed in a concentration of 50% by weight with the thermoplastic resin, preferably a liquid that can form a uniform solution at a temperature of 100.0° C. or higher and 250.0° C. or lower, further preferably a liquid that can form a uniform solution at a temperature of 120.0° C. or higher and 200.0° C. or lower. When a liquid that provides uniform dissolution at a temperature of less than 100.0° C. is used as the contact liquid, the composition solution including the thermoplastic resin and the plasticizer is inhibited from being cooled and solidified to thereby result in the following disadvantage: moldability is degraded, an excess thick coarse structure layer is made, or the pore size is too large. A liquid that cannot form a uniform solution at a temperature of less than 250.0° C. less dissolves the thermoplastic resin to make it difficult to form a sufficiently thick coarse structure layer. The non-volatile liquid is here a liquid having a boiling point higher than 250.0° C. at 1 atm (101325 Pa).

For example, when a polyvinylidene fluoride resin is selected as the thermoplastic resin, phthalic acid esters, adipic acid esters and sebacic acid esters having an ester chain of 7 or less carbon atoms, phosphoric acid esters and citric acid esters having an ester chain of 8 or less carbon atoms, and the like can be suitably used, and in particular, diheptyl phthalate, dibutyl phthalate, diethyl phthalate, dimethyl phthalate, dibutyl adipate, dibutyl sebacate, tri(2-ethylhexyl) phosphate, tributyl phosphate, tributyl acetylcitrate, and the like can be suitably used.

Exceptionally, a plasticizer having a cyclic structure such as a phenyl group, a cresyl group or a cyclohexyl group in the ester chain, namely, dicyclohexyl phthalate (DCHP), diamyl phthalate (DAP), triphenyl phosphate (TPP), diphenylcresyl phosphate (CDP), tricresyl phosphate (TCP), and the like, however, are not preferable because of low ability thereof to form a coarse structure layer.

The temperature of the contact liquid to be used for introducing a coarse structure layer is 100.0° C. or higher, preferably 120.0° C. or higher, which are not higher than the temperature of the uniform solution of the thermoplastic resin and the plasticizer, and is further preferably 130.0° C. or higher, which is not higher than (the temperature of the uniform solution of the thermoplastic resin and the plasticizer−10.0° C.). A temperature of the contact liquid, of lower than 100.0° C., less dissolves the thermoplastic resin, and thus tends to make it difficult to form a sufficiently thick coarse structure layer. A temperature of the contact liquid, of higher than the temperature of the uniform solution of the thermoplastic resin and the plasticizer, causes moldability to be degraded.

Furthermore, in the case of a hollow fiber membrane, transfer of heat may occur in passing of the contact liquid through an annular spinneret, to thereby generate the temperature variation in the annular spinneret, resulting in an ununiform membrane structure in the circumferential direction of the hollow fiber. For example, when the contact liquid at a low temperature is introduced from the lateral of the annular spinneret, the temperature of the annular spinneret is decreased on a part where the contact liquid is introduced, and the pore size of a membrane part formed from the composition including the thermoplastic resin and the plasticizer, which passes through such a part at a relatively low temperature, is decreased to thereby increase the ununiformity of the membrane structure in the circumferential direction. In order to obtain a uniform membrane structure in the circumferential direction of a hollow fiber, it is preferable to achieve a uniform temperature of the spinneret, and in order to achieve this, it is preferable to (1) introduce the contact liquid from the upper portion of the annular spinneret in order to achieve a uniform influence of the temperature of the contact liquid in the circumferential direction of a hollow fiber, and/or (2) decrease the difference between the temperature of the annular spinneret and the temperature of the contact liquid immediately before introduction to the annular spinneret in order to decrease heat transfer between the annular spinneret and the contact liquid. In (2), the difference between the temperature of the annular spinneret and the temperature of the contact liquid immediately before introduction to the annular spinneret is preferably 80.0° C. or lower. A difference in temperature of higher than 80.0° C. may cause an ununiform membrane structure in the circumferential direction to be formed, resulting in virus leakage in an increase in the total amount of viruses to be loaded to the virus removal membrane.

In order to decrease the difference between the temperature of the annular spinneret and the temperature of the contact liquid, various methods such as a method of utilizing temperature modulation in the vicinity of the spinneret and a method of decreasing the temperature of the composition including a plastic resin and the plasticizer can be considered, and a method of controlling the temperature of the contact liquid in introduction of the contact liquid to the spinneret, to a high temperature, is preferable.

When a coarse structure layer is introduced on only one surface of the microporous membrane, a method of cooling other surface corresponding to a dense structure layer can be performed according to a conventional method. That is, the membrane can be cooled with being in contact with a thermal conductor. As the thermal conductor, a metal, water, air or the plasticizer itself can be used. Specifically, a method can be utilized which includes extruding the uniform solution including the thermoplastic resin and the plasticizer in the form of a sheet through a T-die or the like, bringing the sheet into contact with a metallic roll for cooling, to form a dense structure layer, and bringing a membrane surface, which is not brought into contact with the roll, into contact with a non-volatile liquid which can partially dissolve the thermoplastic resin, to thereby form a coarse structure layer. A method can also be utilized which includes extruding the uniform solution of the resin and the plasticizer in the form of a cylinder or hollow fiber through a circular die, an annular spinneret or the like, allowing the liquid, which can partially dissolve the thermoplastic resin, to pass through the inside of the cylinder or hollow fiber, to thereby form a coarse structure layer on the inner surface, and bringing the outside into contact with a cooling medium, such as water, for cooling, to thereby form a dense structure layer.

In order to form a homogeneous dense structure layer small in pore size in the method of producing the microporous membrane according to the embodiment, the cooling rate in cooling and solidifying is preferably sufficiently high. The cooling rate is preferably 50.0° C./min or more, more preferably 100.0 to $1.0 \times 10^{5}$° C./min, further preferably 200.0 to $2.0 \times 10^{4}$° C./min. A method of bringing into contact with a metallic cooling roll or water is suitably used as a specific method, and in particular, a method of bringing into contact with water is preferable because of being capable of achieving rapid cooling by evaporation of water.

The temperature of the medium for cooling and solidifying is not generally determined and is preferably low depending on the molecular weight of the polymer. For example, in the case of bringing into contact with water, the temperature of water is 50.0° C. or lower, more preferably 40.0° C. or lower, more preferably 30.0° C. or lower. A lower temperature of the medium for contact tends to result in a higher bubble point of a membrane to be formed, and is thus preferable because a high virus removal capability can be maintained even in the case of (1) decreasing the pressure (flow velocity) level, (3) temporarily interrupting filtration to perform repressurizing (Stop & start), or (2) temporarily interrupting filtration after filtration of a pharmaceutical protein, for washing with a Buffer (Post-wash), in particular, in use of a virus removal filter.

In the manufacturing method according to the embodiment, the composition including the thermoplastic resin and the plasticizer and uniformly heated to dissolve is preferably allowed to pass through an air gap after being discharged through the discharge port and before being cooled and solidified. The surface layer of the polymer solution discharged is cooled and a part of the plasticizer is gasified in the air gap to thereby form a densest layer as a densest layer on the surface layer portion. The length of the air gap is preferably 10 mm or more and 300 mm or less, further preferably 30 mm or more and 200 mm or less.

When the length of the air gap is within the above range, a smaller air gap provides a dense layer larger in thickness and a larger air gap provides a dense layer larger in thickness. As long as the length is within the above range, a membrane having high virus removal performance and high filtration efficiency can be manufactured.

Furthermore, in the manufacturing method according to the embodiment, a gas release portion may be provided in the air gap part in order to remove the plasticizer gasified, but it is here necessary to pay attention to the flow of air to the composition discharged. When there is variation in the flow of air contacted to the composition discharged, variation in the temperature of the composition can be generated to consequently cause local variation in structure to be generated. For example, when the composition discharged is in the form of a hollow fiber, an opposite portion to the gas release portion is more cooled due to the flow of air in gas release from the lateral of the composition, to thereby easily provide a denser structure, resulting in variation in the structure in the circumferential direction. Accordingly, the gas release portion is preferably provided so as to uniform the flow of air with respect to the composition discharged. Specifically, upward gas release or downward gas release is preferably adopted so that the flow of air is in parallel with the composition discharged.

In the case of lateral gas release, the rate of air to be contacted to the composition is preferably 10 m/s or less, preferably 7 m/s, 5 m/s, 3 m/s or less, more preferably 1 m/s or less.

In step (b) of removing a substantial part of the plasticizer from the membrane formed, an extraction solvent is used for removing the plasticizer. The extraction solvent preferably serves as a poor solvent to the thermoplastic resin and a good solvent to the plasticizer, and preferably has a boiling point lower than the melting point of the microporous membrane. Examples of such an extraction solvent include hydrocarbons such as hexane and cyclohexane, halogenated hydrocarbons such as methylene chloride and 1,1,1-trichloroethane, alcohols such as ethanol and isopropanol, ethers such as diethyl ether and tetrahydrofuran, ketones such as acetone and 2-butanone, or water.

In the embodiment, a first method of removing the plasticizer from the membrane is performed by immersing the microporous membrane cut out to a predetermined size in a vessel in which the extraction solvent is accommodated, sufficiently washing the microporous membrane, and then drying off the solvent attached, by air or hot air. Here, it is preferable to repeatedly perform the immersion operation and the washing operation several times because the plasticizer remaining in the microporous membrane is decreased. In addition, it is preferable to hold the end of the microporous membrane in order to inhibit the microporous membrane from being shrunk during a series of immersion, washing and drying off operations.

A second method of removing the plasticizer from the membrane is performed by continuously sending the microporous membrane in a tank filled with the extraction solvent, immersing the microporous membrane in the tank over a time sufficient for removal of the plasticizer, and drying off the solvent attached thereafter. Here, it is preferable for an enhancement in extraction efficiency to apply a known procedure such as a multistage method of dividing the interior of the tank to a multistage to sequentially send the microporous membrane to respective tanks with a difference in concentration, or a counterflow method of feeding the extraction solvent in an opposite direction to the traveling direction of the microporous membrane to provide the concentration gradient. In both the first and second methods, it is important to substantially remove the plasticizer from the microporous membrane. The substantial removal means removal of the plasticizer in the microporous membrane to such an extent that performance as a separation membrane is not impaired, and the amount of the plasticizer remaining in the microporous membrane is preferably 1% by weight or less, further preferably 100 ppm by mass or less. The amount of the plasticizer remaining in the microporous membrane can be quantitatively determined by gas chromatography, liquid chromatography or the like. In addition, it is further preferable to warm the extraction solvent at a temperature lower than the boiling point of the solvent, preferably a temperature in the range of (boiling point-5.0° C.) or lower because diffusion of the plasticizer and the solvent can be promoted to result in an enhancement in extraction efficiency.

A microporous membrane made of a hydrophobic resin excellent in physical strength is excellent as compared with a microporous membrane made of a hydrophilic resin such as cellulose, from the viewpoint of being capable of withstanding a high filtration pressure, but causes adsorption of proteins and the like, and contamination, clogging and the like of the membrane to easily occur, resulting in a rapid reduction in filtration rate. Therefore, when the microporous membrane made of a hydrophobic resin is used, hydrophilicity is imparted to the membrane in order to prevent occlusion due to adsorption of proteins and the like. In the manufacturing method according to the embodiment, it is preferable to introduce hydrophilic functional groups on the pore surface of the hydrophobic membrane by a graft polymerization method to reduce adsorption property of proteins and the like. The reason for this is because the graft polymerization method can uniformly hydrophilize not only a large pore but also a small pore and can equally hydrophilize not only the inner surface of the membrane but also the outer surface thereof without any variation, as compared with other methods (for example, a method of blending a hydrophilic polymer and a method of coating with a hydrophilic polymer).

In addition, graft polymerization is preferable because hydrophilicity is imparted by chemical bonds and therefore elution in a treatment liquid can less occur as compared with other methods. The graft polymerization method means a reaction in which radicals are generated in a polymer microporous membrane by a procedure such as an ionizing radiation or a chemical reaction and the radicals act as starting points to graft polymerize monomers in the membrane.

In the embodiment, any procedure can be adopted in order to generate radicals in the polymer microporous membrane, but irradiation with an ionizing radiation is preferably adopted in order to uniformly generate radicals in the entire membrane. With respect to the type of the ionizing radiation, a γ-ray, an electron beam, a β-ray, a neutron ray, and the like can be utilized, and an electron beam or a γ-ray is most preferable in industrial scale implementation. An ionizing radiation is obtained from a radioisotope such as cobalt 60, strontium 90 or cesium 137, or X-ray equipment, an electron beam accelerator, an ultraviolet ray irradiation apparatus or the like.

The exposure dose of an ionizing radiation is preferably 1 kGy or more and 1000 kGy or less, more preferably 2 kGy or more and 500 kGy or less, most preferably 5 kGy or more and 200 kGy or less. An exposure dose of less than 1 kGy does not uniformly generate radicals, and an exposure dose of more than 1000 kGy may cause the membrane strength to be reduced.

A graft polymerization method by irradiation with an ionizing radiation is generally roughly classified to a preirradiation method including generating radicals in a membrane, and then bringing the radicals into contact with a reactive compound, and a coincidence irradiation method including generating radicals in a membrane in the state where the membrane is in contact with reactive compounds. In the embodiment, any method can be applied and a preirradiation method is more preferable because oligomers are less produced.

In the embodiment, hydrophilic vinyl monomers having one vinyl group as the reactive compound, and if necessary crosslinking agents are used, and brought into contact with a polymer microporous membrane in which radicals are generated. The contact method can be performed in any of a gas phase and a liquid phase, but a method of performing such contact in a liquid phase that allows a graft reaction to uniformly progress is preferable. In order to allow a graft reaction to further uniformly progress, when hydrophilic vinyl monomers having one vinyl group are dissolved in a solvent in advance and crosslinking agents are then used, the hydrophilic vinyl monomers and the crosslinking agents are preferably dissolved in a solvent in advance and then brought into contact with the polymer microporous membrane.

As described above, in the method of producing a hydrophilic microporous membrane according to the embodiment, the hydrophilic vinyl monomers having one vinyl group are graft polymerized in the polymer microporous membrane to impart hydrophilicity onto the pore surface, reducing adsorption of physiologically active substances such as proteins. The hydrophilic vinyl monomers having one vinyl group in the embodiment are monomers having one vinyl group, which are uniformly dissolved when mixed in a concentration of 1% by vol with pure water at 25.0° C. under the atmospheric pressure. Examples of the hydrophilic vinyl monomers include vinyl monomers having a hydroxyl group or a functional group serving as a precursor thereof, such as hydroxypropyl acrylate and hydroxybutyl acrylate, vinyl monomers having an amide bond, such as vinylpyrrolidone, vinyl monomers having an amino group, such as acrylamide, vinyl monomers having a polyethylene glycol chain, such as polyethylene glycol monoacrylate, vinyl monomers having an anion exchange group, such as triethylammoniumethyl methacrylate, and vinyl monomers having a cation exchange group, such as sulfopropyl methacrylate.

In the embodiment, among the above hydrophilic vinyl monomers, vinyl monomers having at least one hydroxyl group or a functional group serving as a precursor thereof are preferably used because of resulting in a reduction in receding contact angle of the membrane. More preferably, esters of an acrylic acid or methacrylic acid and a polyhydric alcohol, such as hydroxypropyl acrylate and 2-hydroxyethyl methacrylate, alcohols having an unsaturated bond, such as allyl alcohol, and enol esters such as vinyl acetate and vinyl propionate are used, and most preferably, esters of an acrylic acid or methacrylic acid and a polyhydric alcohol, such as hydroxypropyl acrylate and 2-hydroxyethyl methacrylate are used. A hydrophilic microporous membrane obtained by grafting of hydroxypropyl acrylate can achieve a low receding contact angle and sufficient globulin permeation performance.

The solvent that dissolves the hydrophilic vinyl monomers having one vinyl group and the crosslinking agents used if necessary is not particularly limited as long as it can uniformly dissolve them. Examples of such a solvent include alcohols such as ethanol, isopropanol and t-butyl alcohol, ethers such as diethyl ether and tetrahydrofuran, ketones such as acetone and 2-butanone, water, or mixtures thereof.

In dissolution of the hydrophilic vinyl monomers having one vinyl group and the crosslinking agents used if necessary, the concentration is preferably 3% by vol to 30% by vol, more preferably 3% by vol to 20% by vol, most preferably 3% by vol to 15% by vol. A concentration of 3% by vol or more is preferable because of imparting sufficient hydrophilicity. A concentration of more than 30% by vol is not preferable because a hydrophilization layer may be embedded in a pore and permeation performance tends to be degraded.

The amount of the reaction liquid in which the hydrophilic vinyl monomers having one vinyl group and the crosslinking agents used if necessary, to be used in graft polymerization, are dissolved in the solvent is preferably $1\times10^{-5}$ m$^3$ to $1\times10^{-3}$ m$^3$ based on 1 g of the polymer microporous membrane. An amount of the reaction liquid of $1\times10^{-5}$ m$^3$ to $1\times10^{-3}$ m$^3$ provides a membrane sufficient in uniformity. The reaction temperature in graft polymerization is generally 20.0° C. to 80.0° C., but not particularly limited.

In the embodiment, a hydrophilization layer suitable for the hydrophobic microporous membrane is introduced to realize high protein permeability. Therefore, the graft ratio thereof to be grafted to the hydrophobic microporous membrane is preferably 3% or more and 50% or less, further preferably 4% or more and 40% or less, most preferably 6% or more and 30% or less. A graft ratio of less than 3% causes hydrophilicity of the membrane to be insufficient, resulting in a rapid reduction in filtration rate along with adsorption of proteins. A graft ratio of more than 50% causes a hydrophilization layer to be embedded in relatively small pores, not resulting in a sufficient filtration rate. The graft ratio here means the value defined by the following expression (6).

Graft ratio (%)=100×{(mass of membrane after grafting−mass of membrane before grafting)/mass of membrane before grafting}     (6)

EXAMPLES (Manufacturing Virus Removal Membrane)

A powder obtained by stirring and mixing a composition including 49% by weight of a polyvinylidene fluoride resin (KF#1300 manufactured by Kureha Corporation) and 51% by weight of dicyclohexyl phthalate (manufactured by Hokko Chemicals Co., Ltd.) by use of a Henschel mixer at room temperature was loaded through a hopper, melt kneaded at 210.0° C. by use of a twin screw extruder (26 mmφ, L/D=50) to uniformly dissolve, thereafter extruded in the form of a hollow fiber at a discharge rate of 4.2 g/min through a spinneret whose temperature was modulated at 225.0° C. and which included a annular orifice having an inner diameter of 0.8 mm and an outer diameter of 1.05 mm, allowed to pass through an air gap, thereafter cooled and solidified in a water bath whose temperature was modulated at a coagulating bath temperature represented in FIG. 5 and FIG. 6, and wound up as a skein at a rate of 50 m/min. Here, dibutyl phthalate (manufactured by Daihachi Chemical Industry Co., Ltd.) as a hollowing agent was allowed to flow in the interior of the hollow fiber at a rate of 7.1 g/min. In Examples 1 to 11 and Comparative Examples 1 to 3, dibutyl phthalate was introduced from the lateral of the spinneret, and the temperature immediately before introduction to the spinneret and the temperature in discharge from the spinneret were as represented in FIG. 5 and FIG. 6. The rate of air to be contacted to the hollow fiber from the lateral in the air gap was 2.7 m/s. Thereafter, dicyclohexyl phthalate and dibutyl phthalate were removed by extraction with 2-propanol (manufactured by Tokuyama Corporation), 2-propanol attached was replaced with water, and thereafter a heat treatment at 125.0° C. was performed by use of a high pressure steam sterilization apparatus in the state of immersion in water for 4 hours. Thereafter, water attached was replaced with 2-propanol, thereafter vacuum drying at 60.0° C. was performed, and thus a hollow fiber microporous membrane was obtained. The process from extraction to drying was performed while the membrane was fixed in a constant length state in order to prevent shrinkage.

Subsequently, the microporous membrane was subjected to a hydrophilization treatment by a grafting method. A reaction liquid was used which was obtained by dissolving hydroxypropyl acrylate (manufactured by Osaka Organic Chemical Industry Ltd.) in an aqueous 25% by vol 3-butanol (special grade, Junsei Chemical Co., Ltd.) solution so that the concentration was 8% by vol, and subjecting the resultant to nitrogen bubbling for 20 minutes with the temperature being held at 45.0° C. First, the microporous membrane was irradiated with at least 25 kGy of a γ-ray using Co 60 as a radiation source while being cooled by dry ice to −60.0° C. or lower, under a nitrogen atmosphere. The membrane after irradiation was left to still stand under a reduced pressure of 13.4 Pa or less for 15 minutes, and thereafter brought into contact with the reaction liquid at 45.0° C. and left to still stand for 1 hour. Thereafter, the membrane was washed with 2-propanol and subjected to vacuum drying at 60.0° C. to thereby provide a microporous membrane. It was confirmed that water spontaneously penetrated in pores when the manufactured membrane was brought into contact with water. The performance evaluation results of the manufactured membrane are represented in FIG. 5 and FIG. 6.

In Examples 1 to 11 and Comparative Examples 1 to 3, the difference between the inlet temperature and the outlet temperature of the hollowing agent, the air gap length, and the coagulating bath temperature were as represented in FIG. 5 and FIG. 6. In only Example 6, dibutyl phthalate was introduced through the center of the spinneret. With respect to other membrane manufacturing conditions, the same conditions were adopted in Examples 1 to 11 and Comparative Examples 1 to 3.

(Evaluation of Virus Removal Membrane Using Gold Colloids)

(1) Preparation of Gold Colloid Solution

Respective solutions including gold colloids having particle sizes of 10, 15, 20, and 30 nm (manufactured by Cytodiagnostics Inc.) were purchased. Next, each of the gold colloid solutions was diluted with distilled water for injection, polyoxyethylene-naphthyl ether (1.59% by vol), and poly(sodium 4-styrenesulfonate) (0.20% by vol) so that the absorbance at the maximum absorption wavelength of the gold colloids of each of the gold colloid solutions, measured by an ultraviolet-visible spectrophotometer UVmini-1240 (manufactured by Shimadzu Corporation), was 0.25.

(2) Filtration of Gold Colloid Solution 40 mL of each of the gold colloid solutions prepared was filtered under a pressure of 196 kPa by the virus removal membrane manufactured in each of Examples and Comparative Examples. The filtration surface area of the virus removal membrane was 0.001 m$^2$.

(3) Measurement of Removal Rate of Gold Colloid by Virus Removal Membrane

With respect to each of the gold colloid solutions, the absorbance A of the gold colloid solution before filtration and the absorbance B of the filtrate, at the maximum absorption wavelength of gold colloids, were measured using an ultraviolet-visible spectrophotometer UVmini-1240 (manufactured by Shimadzu Corporation), and the logarithmic removal rate (LRV) of gold colloid by the virus removal membrane according to each of Examples and Comparative Examples, given by the following expression (7), was calculated. The results are represented in FIG. 5 and FIG. 6.

$$LRV = \log_{10}(A/B) \quad (7)$$

(4) Measurement of Uniformity of Gold Colloid Capture Portion

A piece (thickness: 8 μm) was cut out from the virus removal membrane according to each of Examples and Comparative Examples after filtration of each of the gold colloid solutions, and the brightness profile at each of 16 points stained by the gold colloids in the cross section of the piece was measured by an optical microscope (Biozero, BZ8100, manufactured by Keyence Corporation). Next, the brightness profile measured was subtracted from a constant (255). Thereafter, a graph with the membrane thickness (percentage) represented on the horizontal axis and variation in the brightness represented on the vertical axis was created, and the area of the spectrum of variation in the brightness presented on the graph was calculated. Furthermore, the value obtained by dividing the standard deviation of the area of the spectrum of variation in the brightness at 16 points by the average of the area of the spectrum of variation in the brightness at 16 points was calculated as the value indicating the variation coefficient of the amount of gold colloids captured on the gold colloid capture portion in the virus removal membrane according to each of Examples and Comparative Examples. The results in flowing of only gold colloids having the diameter of 20 nm are represented in FIG. 5 and FIG. 6. The virus removal membrane according to each Example tended to be low in variation coefficient as compared with the virus removal membrane according to each Comparative Example. Accordingly, it was indicated that uniformity of the amount of gold colloids captured on the gold colloid capture portion of the virus removal membrane according to each Example was high. In addition, among Examples, as the difference between the inlet temperature and the outlet temperature of the hollowing agent before and after the contact with the uniform solution of the thermoplastic resin and the plasticizer was smaller, uniformity of the amount of gold colloids captured on the gold colloid capture portion tended to be higher, and when the hollowing agent was loaded through the center of the spinneret, uniformity of the amount of gold colloids captured on the gold colloid capture portion tended to be higher.

(5) Measurement of Thickness of Gold Colloid Capture Portion

A piece (thickness: 8 μm) was cut out from the virus removal membrane in a wet state with which the respective solutions of the gold colloids having diameters of 20 and 30 nm were filtered. The brightness profile at each of 16 points stained by the gold colloids in the cross section of the piece in a wet state was measured by an optical microscope (Biozero, BZ8100, manufactured by Keyence Corporation). Here, the first distance "a" from the primary surface of the virus removal membrane to a part where the gold colloids were captured and where was closest to the primary surface was measured in the thickness direction. In addition, the second distance "b" from the primary surface of the virus removal membrane to a part where the gold colloid were captured and where was closest to the secondary surface was measured in the thickness direction.

Next, the value A (=a/c (expressed in percentage)) obtained by division of the first distance "a" by the thickness "c" of the virus removal membrane in a wet state and expressed in percentage was calculated at each of 16 points, and the average of the value "A" at 16 points was calculated as the first attainment level. In addition, the value "B" (=b/c (expressed in percentage)) obtained by division of the second distance "b" by the thickness "c" of the virus removal membrane in a wet state and expressed in percentage was calculated at each of 16 points, and the average of the value "B" at 16 points was calculated as the second attainment level.

Furthermore, as represented by the following expression (8), the value obtained by multiplication of the difference between the average "$B_{20}$" of the second attainment level in the virus removal membrane applied to capturing of the gold colloids having the diameter of 20 nm by filtration, and the average "$A_{30}$" of the first attainment level in the virus removal membrane applied to capturing of the gold colloids having the diameter of 30 nm by filtration, by the average "$C_{AVE}$" of the average "$C_{20}$" of the thickness of the virus removal membrane in a wet state applied to capturing of the gold colloids having the diameter of 20 nm by filtration and the average "$C_{30}$" of the thickness of the virus removal membrane in a wet state applied to capturing of the gold colloids having the diameter of 30 nm by filtration was calculated as the thickness "T" of the gold colloid capture portion of the virus removal membrane. The thickness "T" of the gold colloid capture portion is also expressed as the thickness "T" of a dense layer of the virus removal membrane. The results are represented in FIG. 5 and FIG. 6. The virus removal membrane according to each Example tended to have a large thickness "T" of the dense layer, which was in the range of 30 μm or less, as compared with the virus removal membrane according to each Comparative Example.

$$T=(B_{20}-A_{30})\times C_{AVE} \quad (8)$$

In the above method, at least two virus removal membranes: the virus removal membrane applied to capturing of the gold colloids having the diameter of 20 nm by filtration and the virus removal membrane applied to capturing of the gold colloids having the diameter of 30 nm by filtration; were used to measure the thickness of the dense layer. Only one virus removal membrane, however, can also be used to measure the thickness of the dense layer. In this case, one virus removal membrane was used to filter a gold colloid solution including gold colloids having both diameters of 20 nm and 30 nm. Alternatively, one virus removal membrane was used to filter a gold colloid solution with a diameter of 20 nm and then filter a gold colloid solution with a diameter of 30 nm.

Thereafter, a piece was cut out from the virus removal membrane with which each of the gold colloid solutions with the diameters of 20 nm and 30 nm was filtered, and the brightness profile at each of 16 points stained by the gold colloids in the cross section of the piece were measured by an optical microscope (Biozero, BZ8100, manufactured by Keyence Corporation). Herein, the first distance "$a_1$" from the primary surface of the virus removal membrane to a part on the gold colloid capture portion where was closest to the primary surface was measured in the thickness direction. In addition, the second distance "$b_1$" from the primary surface of the virus removal membrane to a part on the gold colloid capture portion where was closest to the secondary surface was measured in the thickness direction.

Next, the value "$A_1$" (=$a_1/c_1$ (expressed in percentage)) obtained by division of the first distance "$a_1$" by the thickness "c" of the wet virus removal membrane and expressed in percentage was calculated at each of 16 points, and the average of the value "$A_1$" at 16 points was calculated as the first attainment level. In addition, the value "$B_1$" (=$b_1/c_1$ (expressed in percentage)) obtained by division of the second distance "$b_1$" by the thickness "c" of the wet virus removal membrane and expressed in percentage was calculated at each of 16 points, and the average of the value "$B_1$" at 16 points was calculated as the second attainment level.

Furthermore, as represented by the following expression (9), the value obtained by multiplication of the difference between the average "$B_1$" of the second attainment level in the virus removal membrane and the average "$A_1$" of the first attainment level in the virus removal membrane, by the average "C" of the thickness of the wet virus removal membrane was calculated as the thickness "T" of the gold colloid capture portion of the virus removal membrane. It was confirmed that no large difference occurred between the thickness "T" calculated by the expression (8) and the thickness "T" calculated by the expression (9).

$$T=(B_1-A_1)\times C \quad (9)$$

(6) Measurement of Thickness of Densest Layer

A piece (thickness: 8 μm) was cut out from the virus removal membrane in a wet state with which a solution of gold colloids having a diameter of 15 nm was filtered. The brightness profile at each of 16 points stained by the gold colloids in the cross section of the piece in a wet state was measured by an optical microscope (Biozero, BZ8100, manufactured by Keyence Corporation). Here, the first distance "d" from the primary surface of the virus removal membrane to a part where the gold colloids were captured and where was closest to the primary surface was measured in the thickness direction. In addition, the second distance "e" from the primary surface of the virus removal membrane to a part where the gold colloids were captured and where was closest to the secondary surface was measured in the thickness direction.

Next, the value "D" (=d/f (expressed in percentage)) obtained by division of the first distance "d" by the thickness "f" of the virus removal membrane in a wet state and expressed in percentage was calculated at each of 16 points, and the average of the value "D" at 16 points was calculated as the first attainment level. In addition, the value "E" (=e/f (expressed in percentage)) obtained by division of the second distance "e" by the thickness "f" of the virus removal membrane in a wet state and expressed in percentage was calculated at each of 16 points, and the average of the value "E" at 16 points was calculated as the second attainment level.

Furthermore, as represented by the following expression (10), the value obtained by multiplication of the difference between the average "E" of the second attainment level and the average "D" of the first attainment level in the virus removal membrane applied to capturing of the gold colloids having the diameter of 15 nm by filtration, by the average "F" of the thickness of the virus removal membrane in a wet state applied to filtration was calculated as the thickness "T" of the 15-nm gold colloid capture portion (densest layer) of the virus removal membrane.

$$T=(E-D)\times F \quad (10)$$

(7) Measurement of particle size dependence property of gold colloid capture portion of virus removal membrane A piece (thickness: 8 μm) was cut out from the virus removal membrane with which the respective gold colloid solutions with the diameters of 15 nm, 20 nm and 30 nm were filtered. The brightness profile at each of 16 points stained by the gold colloids in the cross section of the piece was measured by an optical microscope (Biozero, BZ8100, manufactured by Keyence Corporation). Here, the first distance "a" from the primary surface of the virus removal membrane to a part where the gold colloids were captured and where was closest to the primary surface was measured in the thickness direction. In addition, the second distance "b" from the primary surface of the virus removal membrane to a part where the gold colloids were captured and where was closest to the secondary surface was measured in the thickness direction.

Next, the value "A" (%) obtained by division of the first distance "a" by the thickness "c" of the wet virus removal membrane and expressed in percentage was calculated at each of 16 points, and the average of the value "A" (%) at 16 points was calculated as the first attainment level. In addition, the value "B" (%) obtained by division of the second distance "b" by the thickness "c" of the wet virus removal membrane and expressed in percentage was calculated at each of 16 points, and the average of the value "B" (%) at 16 points was calculated as the second attainment level. The average of the first attainment level and the average of the second attainment level with respect to each of respective gold colloids having the diameters of 15 nm, 20 nm and 30 nm are represented in FIG. 5 and FIG. 6. In FIG. 5 and FIG. 6, numerical values on the left each represent the average of the first attainment level, and numerical values on the right each represent the average of the second attainment level. The capture position of each of respective gold colloids having the diameters of 30 nm, 20 nm and 15 nm was consistently measured with respect to the gold colloids captured by the membrane, and gold colloids not captured by the membrane were not subjected to such measurement.

(Virus Removal Ability of Virus Removal Membrane)

(1) Preparation of Virus-Containing Protein Solution

A polyclonal antibody (human IgG) (Venoglobulin-IH, manufactured by Benesis Corporation) was used to provide an antibody solution that was diluted with water for injection (Otsuka Pharmaceutical Co., Ltd.) so as to have an antibody concentration of 10 mg/mL. The salt concentration was adjusted to 0.1 mol/L by use of an aqueous 1 mol/L NaCl solution. Furthermore, the hydrogen-ion exponent (pH) was adjusted to 4.0 by use of 0.1 mol/L HCl or 0.1 mol/L NaOH, to provide a protein solution. Porcine parvovirus (PPV; Japanese Association of Veterinary Biologics) in a concentration of 1.0% by vol was added to the resulting protein solution, and the solution was well stirred to provide a virus-containing protein solution.

(2-1) Filtration (Normal) of Virus-Containing Protein Solution

The virus removal membrane manufactured, having a membrane area of 0.001 m², was used at a filtration pressure of 196 kPa to perform dead-end filtration of the virus-containing protein solution until the amount of filtration reached 150 L/m².

(2-2) Filtration (Pressure Release) of Virus-Containing Protein Solution

The virus removal membrane manufactured, having a membrane area of 0.001 m², was used at a filtration pressure of 196 kPa to perform dead-end filtration of the virus-containing protein solution until the amount of filtration reached 100 L/m². Thereafter, the filtration was stopped, and the pressure in the virus removal membrane was released, followed by leaving the membrane still standing for three hours while the solution in the virus removal membrane was held. Thereafter, the filtration was resumed at a filtration pressure of 196 kPa, and dead-end filtration of the virus-containing protein solution was performed until the amount of filtration reached 50 L/m². In the present evaluation, the virus removal rate was measured with respect to the filtrate pool before pressure release and after pressure release and repressurizing.

(2-3) Filtration of Virus-Containing Protein Solution (Capture Capacity)

The virus removal membrane manufactured, having a membrane area of 0.001 m², was used at a filtration pressure of 196 kPa to perform dead-end filtration of the virus-containing protein solution. The filtration pressure was measured by a pressure gauge disposed close to a feed solution vessel. The filtrate was taken by 15 L/m², and the filtration was performed until the amount of viruses loaded reached at most 14.0 ($Log_{10}(TCID_{50}/m^2)$).

(3) Measurement of Virus Removal Rate

PK-13 cells (ATCC No. CRL-6489) obtained from American Type Culture Collection (ATCC) were prepared and cultured. In addition, a mixed liquid of 3% by vol of bovine serum (manufactured by Upstate) heated in a water bath at 56.0° C. for 30 minutes and inactivated, and D-MEM (manufactured by Invitrogen Corporation, high glucose) containing 1% by vol of penicillin/streptomycin (+10000 Units/mL penicillin, +10000 µg/mL streptomycin, manufactured by Invitrogen Corporation) were prepared. Hereinafter, the mixed liquid is referred to as "3% by vol FBS/D-MEM". Next, the PK-13 cells were diluted with 3% by vol FBS/D-MEM to prepare a diluted cell suspension having a cell concentration of $2.0 \times 10^5$ (cells/mL). Next, ten 96-well round-bottom cell culture plates (manufactured by Falcon Corporation) were prepared, and the diluted cell suspension was dispensed to all wells by 100 µL.

Each of the filtrate of the virus-containing protein solution, 10-fold, $10^2$-fold, $10^3$-fold, $10^4$-fold and $10^5$-fold diluted solutions of the filtrate, and $10^2$-fold, $10^3$-fold, $10^4$-fold, $10^5$-fold, $10^6$-fold and $10^7$-fold diluted solutions of the virus-containing protein solution not filtered was dispensed to every eight wells of each of the cell culture plates, to which the diluted cell suspension was dispensed, by 100 µL. Thereafter, each of the cell culture plates was placed in an incubator at 37.0° C. in a 5% carbon dioxide atmosphere, and the cells were cultured for 10 days.

The cell cultured for 10 days was subjected to 50% tissue culture infectious dose (TCID50) measurement by use of the erythrocyte adsorption method (see Experimental Study of Viruses, General, edited by National Institute of Infectious Diseases, p. 173) described below. First, preserved chicken blood (manufactured by Nippon Bio-Test Laboratories Inc.) was diluted 5-fold with PBS (−) (manufactured by Nissui Pharmaceutical Co., Ltd.; prepared by the method described in the instruction attached to the product) and then centrifuged at 2500 rpm at 4.0° C. for five minutes to precipitate erythrocytes. Thereafter, the supernatant was removed by aspiration, and the resulting erythrocyte-containing precipitate was diluted again 200-fold with the PBS (−).

Next, the PBS (−) diluted solution of the erythrocyte precipitate was dispensed by 100 µL to all wells of the cell culture plates, and left to still stand for two hours. Thereafter, the presence of the adsorption of erythrocytes to the surface of the cellular tissue cultured was visually confirmed, and a well where the adsorption was confirmed was counted as a well with viral infection and a well where the adsorption was not confirmed was counted as a well without viral infection. Furthermore, the degree of viral infection was confirmed every well, to which each of the filtrate of the virus-containing protein solution and the diluted solutions of the filtrate, and the diluted solutions of the virus-containing protein solution not filtered was dispensed, the $\log_{10}$ ($TCID_{50}$/mL) was calculated as an infectivity titer according to the Reed-Muench method (see Experimental Study of Viruses, General, edited by National Institute of Infectious Diseases, p. 479-480), and the logarithmic removal rate (LRV) of virus was calculated using the following expressions (11) and (12). The results are represented in FIG. 5 and FIG. 6.

$$LRV = \log_{10}(C_0/C_F) \quad (11)$$

In the expression, $C_0$ represents the infectivity titer of the virus-containing protein solution not filtered (virus-containing protein solution) before filtration by the virus removal membrane, and $C_F$ represents the infectivity titer of the filtrate after filtration by the virus removal membrane.

LRV of process including pressure release (Stop & Start):

$$LRV=\log_{10}(C_0 \times 150/(C_{F100} \times 100 + C_{F50} \times 50)) \quad (12)$$

In the expression, $C_0$ represents the infectivity titer of the virus-containing protein solution not filtered (virus-containing protein solution) before filtration by the virus removal membrane, $C_{F100}$ represents the infectivity titer of the filtrate pool after filtration (100 mL/0.001 m$^2$) by the virus removal membrane before pressure release, and $C_{F50}$ represents the infectivity titer of the filtrate pool after the virus removal membrane being subjected to pressure release, thereafter being left to stand for three hours, and being repressurized to perform filtration (50 mL/0.001 m$^2$).

(4) Calculation of Maximum Capture Capacity

The maximum capture capacity of the virus removal membrane was calculated from the amount of filtration (=maximum filtration capacity), at which a value more than the detection limit was obtained in measurement of the virus removal rate, by the calculation method according to the following expression (13).

$$\text{Maximum capture capacity}(\log_{10}(\text{TCID}_{50}/m^2))=\text{infectivity titer of virus-containing protein solution not filtered}(\log_{10}((\text{TCID}_{50}/\text{mL}) \times \text{maximum filtration capacity}(L/m^2) \times 1000)) \quad (13)$$

A maximum capture capacity of 10.0 raised to the power of 11.5 or more is preferable because the virus removal rate is not reduced even if the amount of viruses to be loaded to the virus removal membrane is increased. Furthermore, a maximum capture capacity of 10.0 raised to the power of 12 or more, 12.5 or more, or 13.0 or more is further preferable.

As represented in FIG. 5 and FIG. 6, the maximum capture capacity was increased in accordance with increases in uniformity and the dense layer thickness.

Evaluation of Flux Decay

The following evaluation was performed with respect to the index of protein filtration performance. A polyclonal antibody (human IgG) (Venoglobulin-IH, manufactured by Benesis Corporation) was used to provide an antibody solution that was diluted with water for injection (Otsuka Pharmaceutical Co., Ltd.) so as to have an antibody concentration of 30 mg/mL. The salt concentration was adjusted to 0.1 mol/L by use of an aqueous 1 mol/L NaCl solution. The pH of the solution was here 4.5. The resulting protein solution was subjected to filtration (150 L/m$^2$) by a virus removal membrane having a membrane area of 0.001 m$^2$ at a filtration pressure of 294 kPa. A filtration rate of 0 to 10 L/m$^2$ at the initial stage of filtration was defined as $F_{10}$, a filtration rate of 140 to 150 L/m$^2$ at the completion of filtration was defined as $F_{150}$, and the flux decay was calculated by the following expression (14).

$$\text{Flux Decay (\%)}=(F_{10}-F_{150}) \times 100/F_{10} \quad (14)$$

(Physical Properties of Virus Removal Membrane)

(1) Outer Diameter and Inner Diameter of Hollow Fiber, and Membrane Thickness

The outer diameter and the inner diameter of a hollow fiber microporous membrane were determined by photographing the torn vertical section of the membrane by a stereoscopic microscope (SCOPEMAN 503 manufactured by Moritex Corporation) at 210-magnification. The membrane thickness was calculated as ½ of the difference between the outer diameter and the inner diameter of the hollow fiber.

(2) Porosity

The volume and the mass of the microporous membrane were measured, and the porosity was calculated from the results obtained, according to the following expression (15).

$$\text{Porosity (\%)}=(1-\text{mass}/(\text{density of resin} \times \text{volume})) \times 100 \quad (15)$$

(3) Pure Water Permeation Rate

The amount of permeation of pure water by constant pressure dead-end filtration at a temperature of 25.0° C. was measured, and the pure water permeation rate was defined according to the following expression (16) from the membrane area, the filtration pressure (0.1 MPa), and the filtration time.

$$\text{Pure water permeation rate}(L/m^2/\text{hrs}/0.1 \text{ MPa})=\text{amount of permeation}/(\text{membrane area} \times \text{filtration time}) \quad (16)$$

(4) Measurement Method of Bubble Point

The bubble point (Pa) determined by the bubble point method according to ASTM F316-86 was measured. As the test liquid for immersion of the membrane, hydrofluoroether having a surface tension of 13.6 mN/m (Novec (registered trademark) 7200 manufactured by 3M) was used. The bubble point was defined as a pressure at which, after one hollow fiber membrane having an effective length of 8 cm was installed in a bubble point measurement apparatus, the pressure close to the hollow portion was gradually increased and the flow rate of a membrane permeation gas reached 2.4E-3 L/min.

(5) Measurement Method of Membrane Thickness (Wet Hollow Fiber)

When the hollow fiber membrane thickness in a wet state was measured in the present Example, a wet hollow fiber in capturing of gold colloids with diameters of 30 nm, 20 nm and 15 nm by filtration (40 L/m$^2$) was subjected to measurement by use of an optical microscope (Biozero, BZ8100, manufactured by Keyence Corporation).

REFERENCE SIGNS LIST

1 primary surface
2 secondary surface
10 virus removal membrane

The invention claimed is:

1. A virus removal membrane for removing viruses from a protein-containing solution,
the virus removal membrane comprising:
a primary surface configured to have the protein-containing solution applied thereto, and
a secondary surface configured to allow a liquid that permeates through a thickness of the virus removal membrane to flow therefrom, wherein,
a body of the virus removal membrane is configured such that,
i) a value obtained by dividing a standard deviation of a value of an area of a spectrum of variation in brightness by an average of the value of the area of the spectrum of variation in the brightness is 0.01 or more and 1.50 or less, wherein the brightness is measured for a cross section of the virus removal membrane after 40 mL of a solution containing gold colloids having a diameter of 20 nm is applied to a filtration area of 0.001 m$^2$ of the primary surface, filtered under a pressure of 196 kPa, and penetrates into the body of the virus removal membrane to allow the virus removal membrane to capture the gold colloids for measurement of brightness; and ii) a thickness of a portion where gold colloids having a diameter of 20 nm or more and 30 nm or less are captured in the cross section of the virus removal membrane in a wet state is 10 μm or more and 28.0 μm or less, wherein the thickness is measured after 40 mL of a solution containing gold colloids having a diameter of 20 nm or more and 30 nm or less is applied to the filtration area of 0.001 m² of the primary surface, filtered under a pressure of 196 kPa, and penetrates into the body of the virus removal membrane, wherein the body of the virus removal membrane is configured such that a portion where gold colloids having a diameter of 30 nm are captured is located at a place corresponding to 15% or more and 60% or less of a thickness of the virus removal membrane from the primary surface in the cross section of the virus removal membrane in a wet state after 40 mL of a solution containing the gold colloids having a diameter of 30 nm is applied to the filtration area of 0.001 m² of the primary surface, filtered under a pressure of 196 kPa, and penetrates into the body of the virus removal membrane, a portion where gold colloids having a diameter of 20 nm are captured is located at a place corresponding to 25% or more and 85% or less of the membrane thickness from the primary surface in the cross section of the virus removal membrane in a wet state after 40 mL of a solution containing the gold colloids having a diameter of 20 nm is applied to the filtration area of 0.001 m² of the primary surface, filtered under a pressure of 196 kPa, and penetrates into the body of the virus removal membrane, and a portion where gold colloids having a diameter of 15 nm are captured is located at a place corresponding to 60% or more and 100% or less of the membrane thickness from the primary surface in the cross section of the virus removal membrane in a wet state after 40 mL of a solution containing the gold colloids having a diameter of 15 nm is applied to the filtration area of 0.001 m² of the primary surface, filtered under a pressure of 196 kPa, and penetrates into the body of the virus removal membrane, wherein each of the solutions containing gold colloids are diluted with distilled water for injection, 1.59% by volume of polyoxyethylene-naphthyl ether, and 0.20% by volume of poly(sodium 4-styrenesulfonate) so that the absorbance at the maximum absorption wavelength of the gold colloids of the solution is 0.25 measured by an ultraviolet-visible spectrophotometer, and the virus removal membrane is formed of a hydrophilized synthetic polymer.

2. The virus removal membrane according to claim 1, wherein the body of the virus removal membrane is configured such that, when 40 mL of a solution containing gold colloids having a diameter of 10 nm is applied to the filtration area of 0.001 m² of the primary surface, filtered under a pressure of 196 kPa, and penetrates into the body of the virus removal membrane, gold colloids having a diameter of 10 nm are not captured, wherein the solution containing gold colloids having a diameter of 10 nm is diluted with distilled water for injection, 1.59% by volume of polyoxyethylene-naphthyl ether, and 0.20% by volume of poly(sodium 4-styrenesulfonate) so that the absorbance at the maximum absorption wavelength of the gold colloids of the solution is 0.25 measured by an ultraviolet-visible spectrophotometer.

3. The virus removal membrane according to claim 1, wherein a logarithmic removal rate of gold colloid having a diameter of 30 nm is 1.00 or more,
 a logarithmic removal rate of gold colloid having a diameter of 20 nm is 1.00 or more,
 a logarithmic removal rate of gold colloid having a diameter of 15 nm is 0.10 or more, and
 a logarithmic removal rate of gold colloid having a diameter of 10 nm is less than 0.10.

4. The virus removal membrane according to claim 1, wherein a pore size of a pore is decreased and is then constant, from the primary surface towards the secondary surface in the cross section of the virus removal membrane, and the virus removal membrane has a densest layer in the vicinity of the secondary surface.

5. The virus removal membrane according to claim 1, wherein a thickness of the membrane is 40.0 μm or more and 60.0 μm or less in a dry state.

6. The virus removal membrane according to claim 1, wherein a bubble point is 1.30 MPa or more and 1.80 MPa or less.

7. The virus removal membrane according to claim 1, wherein a ratio of a bubble point (MPa) to a surface tension (N/m) is 96 or more and 133 or less.

8. The virus removal membrane according to claim 1, wherein a pure water permeation rate is 30 L/m²/hrs/0.1 MPa, or more and 80 L/m²/hrs/0.1 MPa, or less.

9. The virus removal membrane according to claim 1, which is a hollow fiber membrane.

10. The virus removal membrane according to claim 1, which is a flat membrane.

11. The virus removal membrane according to claim 1, comprising a thermoplastic crystalline polymer.

12. The virus removal membrane according to claim 1, comprising a hydrophilic graft chain.

13. The virus removal membrane according to claim 1, wherein the body of the virus removal membrane is configured such that, when the solution containing gold colloids having the diameter of 15 nm is applied to the primary surface and penetrates into the body of the virus removal membrane, a thickness of a portion where gold colloids having a diameter of 15 nm are captured in a cross section of the virus removal membrane in a wet state is 2 μm or more and 10 μm or less.

14. The virus removal membrane according to claim 1, further comprising: the body of the virus removal membrane being cooled and solidified by bringing the virus removal membrane into contact with water having a temperature of 30.0° or less.

15. The virus removal membrane according to claim 1, wherein the body of the virus removal membrane is a hollow fiber membrane having a uniform structure in the circumferential direction.

16. The virus removal membrane according to claim 1, wherein the thickness of the portion where the gold colloids having the diameter of 20 nm or more and 30 nm or less are captured in the cross section of the virus removal membrane in the wet state is 26.4 μm or less.

* * * * *